(12) United States Patent
Hanson et al.

(10) Patent No.: US 7,803,757 B2
(45) Date of Patent: Sep. 28, 2010

(54) PEPTIDES BASED ON THE SEQUENCE OF HUMAN LACTOFERRIN AND THEIR USE

(75) Inventors: Lars A. Hanson, Göteborg (SE); Lars Baltzer, Göteborg (SE); Inger Mattsby-Baltzer, Göteborg (SE); Gunnar T. Dolphin, Göteborg (SE)

(73) Assignee: PharmaSurgics in Sweden AB, Göteborg (SE)

( * ) Notice: Subject to any disclaimer, the term of this patent is extended or adjusted under 35 U.S.C. 154(b) by 491 days.

(21) Appl. No.: 11/819,901

(22) Filed: Jun. 29, 2007

(65) Prior Publication Data

US 2008/0299180 A1    Dec. 4, 2008

Related U.S. Application Data

(63) Continuation of application No. 09/743,107, filed as application No. PCT/SE99/01230 on Jul. 6, 1999, now Pat. No. 7,253,143.

(30) Foreign Application Priority Data

Jul. 6, 1998  (SE) .................... 9802441
Jul. 17, 1998 (SE) .................... 9802562
Dec. 29, 1998 (SE) .................... 9804614

(51) Int. Cl.
C07K 14/00 (2006.01)
A61K 38/00 (2006.01)

(52) U.S. Cl. .............. 514/2; 514/11; 514/12; 514/13; 530/300; 530/317; 530/324; 530/326; 530/327; 424/9.1

(58) Field of Classification Search .......... 530/326, 530/317, 324, 327, 300; 514/11, 12, 2, 13; 424/9.1
See application file for complete search history.

(56) References Cited

U.S. PATENT DOCUMENTS 5,304,633 A    4/1994   Tomita et al.
5,565,425 A    10/1996  Yamamoto et al.

FOREIGN PATENT DOCUMENTS

| EP | 0629347 | 12/1994 |
|---|---|---|
| JP | 07-145196 | 6/1995 |
| JP | 07-274970 | 10/1995 |
| JP | 07-309771 | 11/1995 |
| JP | 08-040925 | 2/1996 |
| JP | 08-073499 | 3/1996 |
| JP | 08-143468 | 6/1996 |
| JP | 09040578 | 2/1997 |
| JP | 09-165342 | 6/1997 |
| WO | 98/06424 | 2/1998 |
| WO | 98/06425 | 2/1998 |

OTHER PUBLICATIONS

D.S. Chapple et al., "A Helical Region on Human Lactoferrin, Its Role in Antibacterial Pathogenesis", Advances in Lactoferrin Research, 1998.
W. Bellamy et al., "Identification of the Bactericidal Doman of Lactoferrin", Biochimica et Biophysica Acta, 1121 (1992) 130-136.
Greene et al., Protective Groups in Organic Synthesis, second ed., 1991, p. 293, published by John Wiley & Son.
Daniel S. Chappel et al.,"*Structure-Function Relationship of Antibacterial Synthetic Peptides Homologous to a Helical Surface Region on Human Lactoferrin Against Escherichia coli Serotype 0111*", Infection & Immunity, 66 2434-2440 (1998).
Edward W. Odell et al., "*Antibacterial Activity of Peptides Homologous to a Loop Region in Human Lactoferrin*", FEBS Letters 382, 175-178 (1996).

*Primary Examiner*—Chih-Min Kam
(74) *Attorney, Agent, or Firm*—Buchanan Ingersoll & Rooney PC

(57) ABSTRACT

The invention relates to new peptides formed of at least seven subsequent amino acids of the amino acids in position 12-40, counted from the N-terminal end, in the sequence constituting human lactoferrin, and preferably modifications thereof. The invention also relates to medicinal products comprising such peptides, especially intended for treatment and prevention of infections, inflammations and tumours. Furthermore, the invention relates to food stuff, e.g. infant formula food, comprising the above mentioned peptides.

20 Claims, 6 Drawing Sheets

PEPTIDES BASED ON THE SEQUENCE OF HUMAN LACTOFERRIN AND THEIR USE

The present application is a continuation of U.S. patent application Ser. No. 09/743,107, filed Aug. 21, 2001, now U.S. Pat. No. 7,253,143, which is a 371 of PCT/SE99/01230, filed Jul. 6, 1999, which claims the benefits of foreign priority of Sweden 9802441-7, filed Jul. 6, 1998; Sweden 9802562-0, filed Jul. 17, 1998; and Sweden 9804614-7, filed Dec. 29, 1998.

FIELD OF THE INVENTION

The present invention relates to new peptides and to use thereof, in particular for treatment and/or prevention of infections, inflammations and/or tumours.

BACKGROUND ART

It has for a long time been known that human milk in several ways is anti-inflammatory due to the fact that it is poor in initiators and mediators of inflammation but rich in anti-inflammatory agents (see e.g. Goldman A. S., et al., Anti-inflammatory properties of human milk, Acta Paediatr. Scand. 75:689-695, 1986). Human milk also contains several soluble anti-infective components, such as lactoferrin (see e.g. Hanson L. A., et al., Protective factors in milk and the development of the immune system, Pediatrics 75:172-176, 1983).

Lactoferrin is a single chain metalbinding glycoprotein with a molecular weight of 77 kd. It has been found that the structural domain of lactoferrin responsible for the bactericidal properties is a pepsin-cleaved fragment called lactoferricin (see e.g. Bellamy W., et al., Identification of the bactericidal domain of lactoferrin, Biochim. Biophys. Acta 1121: 130-136, 1992, and Bellamy W., et al., Antibacterial spectrum of lactoferricin B, a potent bactericidal peptide derived from the N-terminal region of bovine lactoferrin, J. Appl. Bact. 73:472-479, 1992).

Lactoferrin receptors are found on many types of cells including monocytes and macrophages, lectin-stimulated human peripheral blood lymphocytes, brush-border cells, and tumour cell lines.

Several patent publications describe the possible use of lactoferrin for treatment of infections or inflammations. In WO 98/06425, e.g., it is disclosed that lactoferrin and lactoferricin can be used for treatment and prevention of infections, inflammations and tumours.

EP-A-0 629 347 describes an antimicrobial agent containing (A) lactoferrin hydrolysate and/or one or more of antimicrobial peptides derived from lactoferrins, and (B) one or more compounds selected from the group consisting of metal-chelating protein, tocopherol, cyclodextrin, glycerine-fatty acid ester, alcohol, EDTA or a salt thereof, ascorbic acid or a salt thereof, citric acid or a salt thereof, polyphosphoric acid or a salt thereof, chitosan, cysteine, and cholic acid as the effective components thereof. This antimicrobial agent is intended for treatment of products, and especially for safely treating e.g. food and medicines. The agent according to this publication is thus a new preservative. In the publication several peptide sequences are given and some of them resemble the peptides according to the invention, although there are several important differences described further below.

Even though native human lactoferrin and lactoferricin have been shown to have desired anti-inflammatory, anti-infectious and anti-tumoural properties they cannot be used clinically on a broad basis since they are very expensive substances due to high production costs.

SUMMARY OF THE INVENTION

The object of the present invention is to provide new peptides which can be used for the same purposes as lactoferrin and/or lactoferricin and which will have the same, or better, effects although being much cheaper to produce.

The aim of the studies leading to the present invention was to design new peptides which could be taken up from the intestines. It has been shown that humans in their brush border membrane have receptors which can bind to human lactoferrin (see e.g. Lonnerdal B., Lactoferrin receptors in intestinal brush border membranes, Adv. Exp. Med. Biol., 1994, 357: 171-175). It has also been shown that bovine lactoferrin does not bind to these receptors. The new peptides should therefore resemble human lactoferrin or human lactoferricin but they should also be easier and especially cheaper to produce. Furthermore, they should be essentially as efficient as, or preferably more efficient than, human lactoferrin or human lactoferricin in treatment and prevention of infections, inflammations and tumours.

It was found that peptides formed of the sequences constituted of all or some of the amino acids 12-40 of human lactoferrin counted from the N-terminal end, and preferably modified versions thereof described further below, have the desired properties.

According to a first embodiment of the invention, it is shown that the peptides formed of the sequences constituted of amino acids 16-40 and amino acids 18-40 from the N-terminal end of human lactoferrin, with some alterations described further below, have the desired properties. Also sequences with only 14 residues, roughly corresponding to residues 18-31 of human lactoferrin wherein C-20 is replaced by A, Q-22 is replaced by K, and N-26 is replaced by D, were found to have the same, and even better, properties.

According to a second embodiment of the invention, it is shown that the peptide formed of the amino acids in positions 12-31, counted from the N-terminal end, in the sequence constituting human lactoferrin, as well as modifications thereof, have the desired properties. Also fragments of this sequence consisting of at least 7 amino acids are shown to have the same, and even better, properties.

According to a third embodiment of the invention it is shown that peptides consisting of 11-17 amino acids corresponding to the sequences that begin with one of the amino acids in positions 15-21 and end with the amino acid in position 31, counted from the N-terminal end, in the sequence constituting human lactoferrin, as well as modifications thereof.

According to a forth embodiment of the invention it is shown that modified peptides consisting of 12 aminoacids based on the sequence consisting of the amino acids in positions 20-31 in human lactoferrin, counted from the N-terminal end, give even better results for the purposes of the present invention.

A plausible mechanism for the uptake of these new peptides in the human body is that the peptides are taken up in the intestine through binding to the above mentioned specific lactoferrin receptors and are then trans-ported through the circulation. However, the invention is in no way limited to this mechanism.

Thus, the present invention relates to new peptides with the sequences given in the appended sequence listing, and to functionally equivalent homologues or analogues thereof.

Furthermore, the invention relates to medicinal products and to food stuff, especially infant formula food, comprising said peptides.

The invention also relates to use of said peptides for the production of medicinal products for treatment and prevention of infections, inflammations and tumours.

The peptides according to the invention are fungicidal and bactericidal, and can thus be used for other applications when substances with such properties are desired. They may for example be used as preservatives.

The characterising features of the invention will be evident from the following description and the appended claims.

DETAILED DESCRIPTION OF THE INVENTION

Thus, the present invention relates to peptides comprising—amino acid based on a fragment of the protein human lactoferrin (hLF). The fragment of hLF that are used as a basis for the invention is constituted by the amino acids in positions 12-40, the sequence of which is:

```
                                             (SEQ. ID. NO. 100)
V-S-Q-P-E-A-T-K-C-F-Q-W-Q-R-N-M-R-K-V-R-G-P-P-V-S-
C-I-K-R
```

In the description single-letter symbols are used to denote the amino acids, while three-letter symbols are used in the appended sequence listing. These symbols, which are well known to man skilled in the art, have the following meaning: A=Ala=alanine, C=Cys=cysteine, D=Asp=aspartic acid, E=Glu=glutamic acid, F=Phe=phenylalanine, G=Gly=glycine, I=Ile=isoleucine, K=Lys=lysine, M=Met=methionine, N=Asn=asparagine, P=Pro=proline, Q=Gln=glutamine, R=Arg=arginine, S=Ser=serine, T=Thr=threonine, V=Val=valine, W=Trp=tryptophan and X=Xaa=a variable amino acid. Ac and $NH_2$ in some of the sequences denote an acetyl ($CH_3CO-$) group and an amino group, respectively, that have been used to modify the amino and the carboxy terminals of the peptides.

The peptides according to the invention may have either of a linear or a cyclic form, which is further explained below.

All the sequences mentioned herein with SEQ. ID. NO. 1-99 are given in the appended sequence listing.

The first embodiment of the invention relates to peptides the sequence of which is:

```
                                             (SEQ. ID. NO. 1)
Ac-X-X-T-K-X-F-X-W-Q-R-X-M-R-K-V-R-X-X-X-X-X-X-X-
X-X-NH2
``` wherein X in position 1 is either E or no amino acid, X in position 2 is either A or no amino acid, X in position 5 is either C or A, X in position 7 is either Q or K, X in position 11 is either N or D, and X in positions 17-25 are either no amino acids at all or -G-P-P-V-S-C-I-K-R. The sequences for the peptides according to the first embodiment of the inventions are SEQ. ID. NO.1-7 in the appended sequence listing.

In a preferred version of the first embodiment of the invention X in position 1 is E, X in position 2 is A, X in position 5 is C, X in position 7 is Q, X in position 11 is N, and X in positions 17-25 are -G-P-P-V-S-C-I-K-R, which gives a peptide the sequence of which is SEQ. ID. NO. 2. The linear form is obtained through protection of the cysteine side chains by acetamidomethyl groups $CH_3 CONHCH_2-$.

Another preferred version of the first embodiment of the invention is a cyclic form of SEQ. ID. NO. 2, obtained by the creation of a disulphide bridge between the two cysteines in positions 5 and 22, resulting in the cyclic peptide the sequence of which is SEQ. ID. NO. 3. The creation of the disulphide bridge has to be performed in a controlled way in order to avoid formation of polymers.

Another preferred version of the first embodiment of the invention is a somewhat shorter peptide wherein X in position 1 in SEQ. ID. NO. 1 is none, X in position 2 is none, X in position 5 is C, X in position 7 is Q, X in position 11 is N, and X in positions 17-25 are -G-P-P-V-S-C-I-K-R, resulting in a peptide the sequence of which is SEQ. ID. NO. 4.

Yet another preferred version of the first embodiment of the invention is a cyclic form of SEQ. ID. NO. 4 obtained by the creation of a disulphide bridge in the same way as for SEQ. ID. NO. 3, resulting in SEQ. ID. NO. 5.

An even more preferred version of this first embodiment of the invention is shorter peptide in which X in position 1 is none, X in position 2 is none, X in position 5 is A, X in position 7 is K, $X_5$ D, and X in positions 17-25 are none, resulting in SEQ. ID. NO. 6.

This peptide may also be modified so that the residues K in position 5 in SEQ. ID. NO. 6 and D in position 9 are linked by the formation of a lactam between the side chains of the residues, thus forming a loop. The sequence of this peptide is SEQ. ID. NO. 7. The lactam formation in this peptide between amino acid chains that are four residues apart in the sequence forces the peptide to F adopt a three-dimensional structure that resembles that of the fragment 18-31 of naturally occurring human lactoferrin and is designed to bind better to the receptor. This peptide with SEQ. ID. NO. 7 is the most preferred peptide according to the first embodiment of the invention.

One advantage of the peptides with SEQ. ID. NO. 6 and SEQ. ID. NO. 7 compared to the other peptides according to the first embodiment of the invention is that they are easier to synthesise and also cheaper per gram since they are shorter.

In all those seven peptides the amino and carboxy terminal ends have been capped, i.e. the free $NH_2$ group at the amino terminal end have been reacted with acetylimidazole to form the amide $CH_3CONH-$ or AcNH— and the free COOH at the carboxy terminal end has been trans-formed into $CONH_2$.

As evident from the sequences above all seven peptides according to the first embodiment of the invention comprise the residues K and R at the carboxy terminal ends. These residues are positively charged under physiological conditions and are capable of strong and specific interactions with receptors. They are therefore an important part of the peptides according to the invention. Also the T residue at the amino terminal end of all of the peptides according to the invention is capable of playing an important part in receptor binding.

The second embodiment of the invention relates to the peptide the sequence of which is:

```
                                             (SEQ. ID. NO. 8)
V-S-Q-P-E-A-T-K-C-F-Q-W-Q-R-N-M-R-K-V-R
``` and fragments thereof consisting of at least 7 amino acids. The sequences for the peptides according to the second embodiment of the inventions are SEQ. ID. NO.8-42 in the appended sequence listing.

The peptides according to this second embodiment of the invention contains at least 7 amino acids. Shorter peptides do not have the desired effects.

A preferred group of peptides according to the second embodiment of the invention are the peptides with SEQ. ID. NO. 9-22 given in the appended sequence listing. The advantage of these peptides, consisting of only seven amino acids each, is that they are relatively short which means that they are cheaper and more easy to produce than the longer peptides according to the invention.

Another preferred group of peptides according to this second embodiment of the invention are the peptides with SEQ. ID. NO. 13 and SEQ. ID. NO. 23-31 in the appended sequence listing, corresponding to modified sequences obtained from the amino acid in position 16 to the amino acid in position 22-31 of human lactoferrin, counted from the N-terminal end.

Yet another preferred group of peptides according to this embodiment are the peptides with SEQ. ID. NO. 22 and SEQ. ID. NO. 31-42 in the appended sequence listing, corresponding to modified sequences obtained from the amino acid in position 13-25 to the amino acid in position 31 of human lactoferrin, counted from the N-terminal end.

The advantage of the peptides according to the second embodiment of the invention is that they form the part of the lactoferricin fragment of the human lactoferrin protein, or a modified version thereof, which the inventors have found to be active with regards to the invention.

The third embodiment of the invention relates to peptides consisting of 11-17 amino acids, comprising the sequence:

```
F-X-W-X-R-X-M-R-K-X-R        (SEQ. ID. NO. 43)
``` or functionally equivalent homologues or analogues thereof. The sequences for the peptides according to the third embodiment of the inventions are SEQ. ID. NO. 43-67 and SEQ. ID. NO. 97 in the appended sequence listing.

In this sequence, the amino acids denoted by X or Xaa are preferably, independently of each other, glutamine (Q or Gln), lysine (K or Lys), aspartic acid (D or Asp), asparagine (N or Asn), or valine (V or Val).

A preferred group of peptides according to the second embodiment of the invention consists of 14 amino acids. Those peptides correspond essentially to the sequence formed by the amino acids in positions 18-31, counted from the N-terminal end, in the sequence constituting human lactoferrin, wherein some amino acids have been modified. The peptides in this group have the sequences SEQ. ID. NO. 6, 7, 50-61 and 98.

The peptide according to this embodiment that mostly corresponds to this part of human lactoferrin is the peptide with SEQ. ID. NO. 50 given in the appended sequence listing. The capped version of this sequence has SEQ. ID. NO. 51.

The amino acid in position 3 in this sequence, i.e. a cysteine (C or Cys) may be replaced by an alanine (A or Ala) or a lysine, the amino acid in position 5, a glutamine, may be replaced by a lysine, the amino acid in position 9, an asparagine, may be replaced by an aspartic acid or a lysine, and the amino acid in position 13, a valine, may be replaced by an aspartic acid.

When the peptide according to this embodiment comprises a cysteine, as the peptides with SEQ. ID. NO. 46-51 and 62-67, it may be advantageous to replace this cysteine by an acetamidomethyl-cysteine in order to avoid that the peptide forms a disulphide bridge with another peptide comprising a cysteine. However, the amino acids glutamine and valine may then not be replaced as described above.

A major advantage of the peptides according to this embodiment is that they form the part, or a modified version of it, of the lactoferricin fragment of the human lactoferrin protein which the inventors have found to be active with regards to the invention.

An other advantage of the peptides according to this embodiment is that they are relatively short which means that they are cheaper and easier to produce than longer peptides, such as lactoferrin itself.

The fourth embodiment of the invention relates to peptides consisting of 12 aminoacids. These peptides are based on a modification of the sequence consisting of the amino acids in positions 20-31 in human lactoferrin, counted from the N-terminal end, corresponding to SEQ. ID. NO. 46. The sequences for the peptides according to the third embodiment of the inventions are SEQ. ID. NO. 68-99 in the appended sequence listing. In the general sequence, SEQ. ID. NO. 99, Xaa in position 3 is preferably Gln or Ala, Xaa in position 4 is preferably Trp or Leu, Xaa in position 5 is preferably Gln, Lys, Orn, Ala or Nle, Xaa in position 6 is preferably Arg, Lys or Ala, Xaa in position 7 is preferably Asn, Orn, Ala, or Nle, Xaa in position 8 is preferably Met or Leu, and Xaa in position 9 is preferably Arg or Lys. In some cases it may be advantageous to let this sequence be proceeded by the sequence Thr-Lys or the longer sequence Glu-Ala-Thr-Lys.

Preferred variants of the fourth embodiment of the invention are SEQ. ID. NO. 70 and SEQ. ID. NO. 74 wherein the amino acid in position 3 and position 7, respectively, in SEQ. ID. NO. 46 has been replaced by an alanine, SEQ. ID. NO. 81 and SEQ. ID. NO. 83 wherein the amino acid in position 6 and position 9, respectively, in SEQ. ID. NO. 46 has been replaced by a lysine, and SEQ. ID. NO. 87 and SEQ. ID. NO. 89 wherein the amino acid in position 5 and position 7, respectively, in SEQ. ID. NO. 46 has been replaced by an ornithine. It is also possible and in some cases preferable, to use capped versions of these sequences according to the invention.

The peptides according to the invention may be either of natural origin, e.g. derived from human lactoferrin, or synthetically produced.

The peptides according to the invention are sometimes "capped", so that the amino and the carboxy terminals of the peptides are turned into amides, as described above. The advantage of the capped versions, i.e. the sequences in which the amino and carboxy terminal ends have been reacted with acetylimidazole to form the amide $CH_3CONH$— or AcNH— and the free COOH at the carboxy terminal end has been transformed into $CONH_2$, is that these peptides are neutral and uncharged and thus has drastically changed electrostatic properties. Assuming that the receptors bind the corresponding sequences of human lactoferrin where there are no N- and C terminal charges, the capped peptides should bind better as they in this respect resemble the native protein more than uncapped peptides. Under physiological conditions at a pH of approximately 7, free amino and carboxy terminals would be ionised and the peptide would thus carry a positive and a negative charge.

In some cases only the capped form of a sequence has been given in the appended sequence listing. However, it is also possible, according to the invention, to use the non-capped forms.

When the peptide according to this embodiment comprises a lysine separated from an aspartic acid or a glutamic acid by three amino acids the lysine and the aspartic acid or the glutamic acid, respectively, may form a lactam, as in SEQ. ID. NO. 54, wherein a lactam is formed between a lysine in position 5 and an aspartic acid in position 9, or as in SEQ. ID. NO. 55 wherein a lactam is formed between a lysine in position 5 and a glutamic acid in position 9. It is also possible to obtain a dilactam, as e.g. in SEQ. ID. NO. 60 and SEQ. ID.

NO. 61, wherein a lactam is formed between a lysine in position 3 and an aspartic acid in position 7 and another lactam is formed between a lysine in position 9 and an aspartic acid in position 13. The lactam formation forces the peptide to adopt a three-dimensional structure that resembles that of the corresponding fragment of human lactoferrin and this may accomplish better binding of the peptide to the lactoferrin receptor.

Apart from the above specified peptides it is also possible to use functionally equivalent homologues or analogues thereof, including those that mimic the three-dimensional structure of the corresponding segment in human lactoferrin due to the introduction of structural constraints such as lactam bridges or other chemical constraints.

The peptides according to the invention are suitable for treatment and/or prevention of infections, inflammations and/or tumours. The term "treatment" used herein refers to curing, reversing, attenuating, alleviating, minimising, suppressing or halting the deleterious effects of a disease state, disease progression or other abnormal condition, and the term "prevention" used herein refers to minimising, reducing or suppressing the risk of developing a disease state or progression or other abnormal or deleterious conditions.

The infections treatable with the peptides or medicinal products according to the invention include infections caused by all kinds of pathogens, such as bacteria, viruses, fungi, etc.

It is also possible to treat different types of inflammations. Inflammation is a complex phenomenon marked i.a. by abnormal "redness" and swelling of tissues and organs, pain and heat in affected areas, capillary dilation, leucocyte infiltration, etc. Inflammation is primarily caused by exposure to bacterial and other noxious agents and physical injury. Inflammation has many forms and is mediated by a variety of different cytokines and other chemical signals. These mediators of inflammation include tumour necrosis factor-$\alpha$ (TNF-$\alpha$), interleukin-1 (IL-1), interleukin-6 (IL-6), interleukin-8 (IL-8), and various colony-stimulating factors (CSFs).

As stated above, the peptides according to the invention are also suitable for treatment of tumours.

The peptides according to the invention may either be used as they are or be included in a medicinal product or a pharmaceutical preparation. The medicinal product or a pharmaceutical preparation according to the invention may also comprise substances used to facilitate the production of the pharmaceutical preparation or the administration of the preparations. Such substances are well known to people skilled in the art and may for example be pharmaceutically acceptable adjuvants, carriers and preservatives.

The peptides or medicinal products according to the invention can be administered to a patient either systemically or locally. The term "patient" used herein relates to any person at risk for or suffering from a disease state, disease progression or other abnormal or deleterious condition.

The systemic administration is suitable e.g. for treatment of urinary tract infection, colitis and tumours. The systemic administration can be undertaken by oral, nasal, intravenous, intraartery, intracavitary, intramuscular, subcutaneous, transdermal, suppositories (including rectal) or other routes known to those of skill in the art. Oral administration is preferred.

The local administration is suitable e.g. for treatment of skin infections, all infections and inflammations in mucosal membranes etc. The local administration can be undertaken by topical, oral, nasal, vaginal or oropharyngal route. For treatment of local infections or inflammations in the skin or mucosal membranes the peptides or medicinal products according to the invention may e.g. be included in a gel, a cream, an ointment, or a paste.

In the method according to the invention an effective amount of a peptide according to the invention is administered to a patient. The term "effective amount" used herein relates an amount sufficient to treat or pre-vent a disease state, disease progression or other abnormal or deleterious conditions.

The peptides or medicinal products and methods according to the invention are particularly well suited for treatment and/or prevention of urinary tract infection and colitis, but several other inflammatory and infectious diseases are also treatable according to the present invention, such as inflammatory bowel diseases, rheumatoid arthritis, conditions caused by the virus HIV-1, conditions caused by the virus CMV, and conditions caused by the fungi *Candida albicans, Candida krusei* and *Cryptococcus neoformans*. This listing is in no way limiting the scope of the invention.

The peptides, medicinal products and methods according to the invention are also well suited for preventive medical care by reducing the risk of developing urinary tract infection or other inflammatory or infectious diseases in patients with an increased risk of attracting such complications.

The peptides, medicinal products and methods according to the invention may either be used alone, in combination with each other or in combination with conventional therapy.

According to the present invention it is also possible to include the peptides, in an effective amount, in any kind of food or beverage intended to reduce infections and/or inflammations in patients running an increased risk of such conditions due to an underlying disease, a low birth weight or a medical treatment. For example, it is possible to include the peptides, in an effective amount, in an infant formula food intended to inhibit harmful effects of bacteria, such as weight loss caused by inflammation induced by bacteria, viruses or fungi in infants. When the peptides according to the invention is to be used in food stuffs, e.g. for nutritional purposes, it is especially preferred to use peptides of natural origin.

Since the peptides according to the invention have antimicrobial effects they can also be used as preservatives in different food stuffs and medicinal products such as gels, creams, ointments, pastes, solutions, emulsions etc.

The invention will now be further explained in the following examples. These examples are only intended to illustrate the invention and should in no way be considered to limit the scope of the invention.

BRIEF DESCRIPTION OF THE DRAWINGS

In the examples below, reference is made to the appended drawings on which.

4A shows the occurrence of occult blood in faeces.

EXAMPLES

Figure 1:
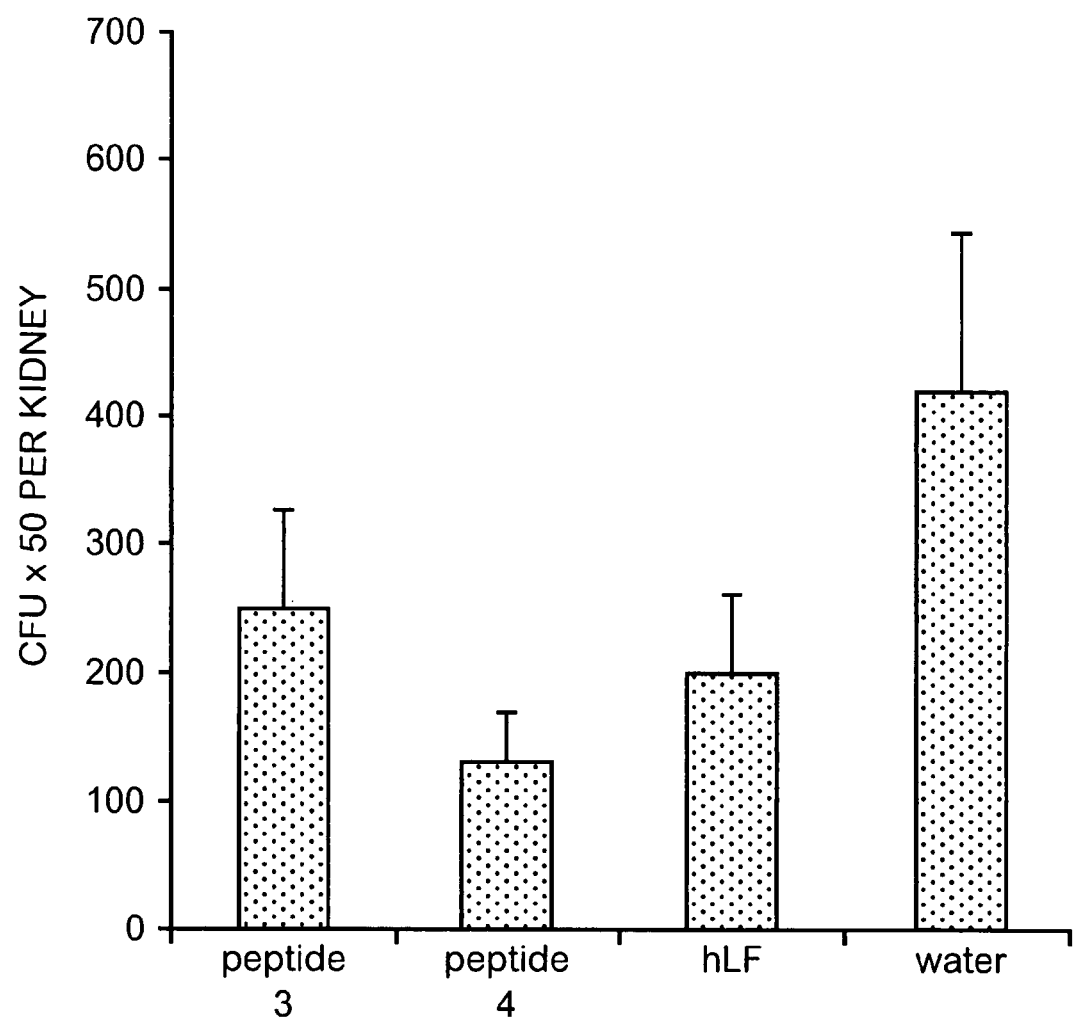
FIG. 1 shows the number of bacteria (CFU) present in kidney in mice with urinary tract infection treated with two peptides according to the invention, peptide 3 and peptide 4, with human lactoferrin, hLF, and with water, respectively.

In the examples below peptide 2 denotes the peptide according to the invention with SEQ. ID. NO. 2, peptide 3 denotes the peptide according to the invention with SEQ. ID. NO. 3, etc.

Morinaga 10, Morinaga 11, Morinaga 12, Morinaga 13, Morinaga 24 and Morinaga 25 denotes the peptides described in EP-A-0 629 347; Morinaga 10 is F-Q-W-Q-R-N (sequence No. 10 in EP-A-0 629 347), Morinaga 11 is F-Q-W-Q-R (sequence No. 11 in EP-A-0 629 347), Morinaga 12 is Q-W-Q-R (sequence No. 12 in EP-A-0 629 347), Morinaga 13 is W-Q-R (sequence No. 13 in EP-A-0 629 347), Morinaga 24 is the cyclic peptide with sequence K-C-F-Q-W-Q-R-N-M-R-K-V-R-G-P-P-V-S-C-I (sequence No. 24 in EP-A-0 629 347), and Morinaga 25 is K-C-F-Q-W-Q-R-N-M-R-K-V-R-G-P-P-V-S-C-I (sequence No. 25 in EP-A-0 629 347).

hLF denotes human lactoferrin.

In the examples, the minimal microbicidal concentrations (MMC) and minimal inhibitory concentrations (MIC) were determined as follows, unless otherwise specified in the examples. Bacterial or fungal strains were cultured in BHI medium over night at 37° C. A volume of the culture was transferred to a new tube with BHI and incubated for two more hours. Thereafter the cells were spun down and the pellet was suspended in BHI medium diluted 1/100 (1% BHI). The concentration of bacterial or fungal cells was spectrophotometrically determined at 650 nm. The microbial concentrations were also determined by viable counts. Peptides serially diluted in 1% BHI by twofold or tenfold steps were added in triplicate to the wells of a microtiterplate (200 μl per well). The bacterial or fungal cell solutions were added in 10 μl volumes to give a final concentration of approximately $1\text{-}5 \times 10^5$ cells per ml in the well. The microplate was incubated at 37° C. in a humid chamber for two hours. Thereafter 5 μl was taken from each well and added as a drop onto a blood agar plate and incubated over night at 37° C. The microplate was incubated for another 20 hours at 37° C. and thereafter analysed spectrophotometrically at 650 nm in a microplate reader (Emax, Molecular Devices, USA). The concentration of peptide causing a 99% reduction of the inoculum after 2 hours of incubation was defined as the $MMC_{99\%}$. The MIC value was defined as the concentration giving no increase in the absorbance value above the background level after 20 hours of incubation.

Example 1

This example illustrates solid phase synthesis of peptide 2, peptide 3, peptide 4 and peptide 5 according to the invention, and also of the peptides Morinaga 24 and Morinaga 25 used in the examples further below.

The syntheses were performed by Fmoc continuos flow strategy on a Biosearch Pioneer automated peptide synthesiser. The peptides were synthesised on a 0.1-0.2 mmol scale with the resins PAC-PEG-PS, 0.21 mmol/g for the peptide acids and Fmoc-PAL-PEG-PS, 0.20 mmol/g for the peptide amides.

The side chains of the peptides according to the invention were protected by piperidine-stable tert-butyl (for serine and threonine), tert-butyl ester (for glutamic acid), tert-butyloxycarbonyl (for lysine and tryptophan), triphenylmethyl (for asparagine, cysteine, glutamine and histidine), acetamidomethyl (for cysteine), and 2,2,4,6,7-pentamethyldihydrobenzofuran-5-sulphonyl (for arginine) groups.

For the peptides Morinaga 24 and Morinaga 25, attachment of isoleucine to the PAC-PEG-PS resin was performed using the isoleucine symmetrical anhydride. The resin (1 g, 0.21 mmol) was allowed to swell in 3 ml dimethyl formamide (DMF). Fmoc-I (10 eq, 2.1 mmol) was dissolved in 5 ml dichloromethane (DMC) and 5 drops of DMF. Diisopropyl carbodiimide (DIPCDI) (5 eq, 1.05 mmol) was added to the amino acid solution after which it was left to stand for 20 min at 0° C. The DCM was removed under reduced pressure and the remaining oil was dissolved in DMF and added to the resin. Dimethylaminopyridine (DMAP) (1 eq) was added to the resin and the slurry was allowed to stand at room temperature with occasional swirling for 1 hour. After washing with DCM the resin was ready for peptide synthesis.

Removal of the α-amino protecting group (Fmoc) was performed with 20% piperidine in DMF for 7 min. All couplings proceeded in DMF, using 4 times excess of activated amino acid over peptide and 4 eq of benzotriazolyl tetramethyluronium tetrafluoborate (TBTU):diisopropyl ethylamine (DIPEA) (1:2, mol/mol). A six fold excess of hydroxybenzotriazole (HOBt) was added to the couplings of the cysteine residues (acetamidomethyl and triphenylmethyl).

Peptide 2, peptide 3, peptide 4, and peptide 5 were acylated at the amino terminus using a 0.3 M solution of acetic anhydride in DMF.

Final deprotection and cleavage of the peptide from the resin was performed for 2 hours at room temperature using a mixture of 9.25 ml trifluoro acetic acid (TFA), 250 μl water, 250 μl ethanedithiol and 250 μl triisopropylsilan per g of peptide resin. The resin was removed by filtration. The peptide was precipitated by use of cold diethylether, centrifuged and resuspended in fresh diethylether two more times to extract the scavengers and TFA. The peptides were dissolved in water and lyophilised.

The cyclisation of the disulphide bonded peptides, peptide 3 and peptide 5, were performed on unpurified material. Approximately 200 mg of peptide was dissolved in 1l of degassed water. Ammonium hydrogen carbonate was added until the pH was in the range of 6-7 and the mixture was left with stirring and air contact for about 1 day, and was finally lyophilised.

The peptides were purified by reversed-phase high-pressure liquid chromatography eluating with isochratic mixtures of isopropanol (12-16% IPA) and 0.1% TFA. Two different columns were used, Microsorb, C-8 41.4×250 mm, 8 μm (column A), and Hichrom, C-8 25×250 mm, 7 μm (column B). The peptides eluated as broad peaks with the retention times (R) given in table 1 below. The identification was done by ES-MS. MW in the table denotes the molecular weight.

Example 2

This example illustrates solid phase synthesis of peptide 6 and peptide 7 according to the invention.

The syntheses were performed as described in example 1 with the following modifications of the synthetic procedure.

The side chains of the lactam forming amino acids K in position 5 and D in position 9 were protected by 1(4,4-dimethyl-2,6-dioxocyclohex-1-ylidene)ethyl (Dde) and 4-{N-[1 (4,4-dimethyl-2,6-dioxocyclohexylidene)-3-methylbutyl]-amino}benzyl ester (ODmab), respectively.

After the synthesis of the capped sequence was completed, the Dde and ODmab groups were removed by 2% hydrazine (v/v) in DMF for 10 min. The resin was washed with DMF, 1M DIPEA in DMF and finally by DMF.

In the case of peptide 7 lactam formation between the side chains was allowed to proceed for 8 hours after the addition of a four fold excess of azabenzotriazolyl tetramethyluronium hexafluorophosphate (HATU):DIEPEA, 1:2 in DMF. The resin was washed with the following solvents/solutions: DMF, 20% piperidine in DMF, methanol and DCM. The resin was dried under vacuum, and the peptide was cleaved from the resin as described above.

Peptide 7 eluated as a broad peak with the retention times (R) given in table 1 below.

TABLE 1

| Peptide | Column | % IPA | Flow (ml/min) | R (min) | MW (found/calc.) |
|---|---|---|---|---|---|
| Peptide 2 | B | 14 | 15 | 11 | 3201/3204.7 |
| Peptide 3 | A | 13 | 80 | 16 | 3057.1/3060.7 |
| Peptide 4 | A | 14 | 80 | 12 | 3002.4/3004.0 |
| Peptide 5 | B | 14 | 15 | 10 | not determined |
| Peptide 7 | B | 12 | 18 | 12 | not determined |
| Morinaga 24 | B | 16 | 15 | 20 | 2575/2576.0 |
| Morinaga 25 | B | 16 | 15 | 18 | 3430/3432.0 |

Example 3

In this example the bactericidal activity of the peptides according to the invention was tested and compared to the bactericidal activity of human lactoferrin.

Human lactoferrin (hLF), peptide 3, and peptide 4, respectively, were incubated with two different strains of *E. coli*, *E. coli* O14 (experiment I) and O6K5 (experiment II), in diluted growth medium (1/100 BHI—brain heart infusion) for 2 hours. The peptides were also incubated with *E. coli* O14 in 0.05 mM KCl (pH 7) without any growth medium (experiment III). Different concentrations of the peptides were tested.

After the incubation, samples were taken for bacterial plating. Serial dilutions of five- and fourfold steps were used in experiments I and II, respectively, and of twofold steps in experiment III.

The concentrations of the different peptides required for killing 100% (experiments I and II) or 90% (experiment III) of the bacteria are given in table 2.

TABLE 2

| Exp. | Agent | Concentration of agent for 100%/90% killing (μg/ml) |
|---|---|---|
| I | hLF | 400 |
| I | peptide 3 | 4.4 |
| I | peptide 4 | 4.4 |
| II | hLF | 2000 |
| II | peptide 4 | ≦7.8 |
| III | hLF | >4000 |
| III | peptide 3 | 12.5 |
| III | peptide 4 | 3.2 |

From table 2 it is evident that the peptides according to the invention were much more efficient as bactericidal agents than human lactoferrin.

Example 4

In this example the fungicidal activity of the peptides according to the invention was tested and compared to the fungicidal activity of human lactoferrin. Different concentrations of hLF, peptide 3 and peptide 4 were incubated with different strains of *Candida albicans* and *Candida krusei* during 1-2 hours at 37° C. in 0.05 mM KCl at pH 7.0 at two different occasions—experiment I and II, respectively. After incubation samples were taken for plating on Saboroud plates. The concentrations of the different peptides required for killing 99% of the fungi are given in table 3.

TABLE 3

| | | Concentration of agent for 99% killing (μg/ml) | | | ratio hLF/ | |
|---|---|---|---|---|---|---|
| Exp. | Candida strain | hLF | peptide 3 | peptide 4 | /pep. 3 | /pep. 4 |
| I | C. albicans ATCC 64549 | >50 | 0.6 | 1.25 | >83 | >40 |
| I | C. albicans CCUG 90028 | >50 | 0.6 | 1.25 | >83 | >40 |
| I | C. krusei CCUG 35849 | 12.5 | 0.6 | 1.25 | 21 | 10 |
| I | C. krusei CCUG 969 | 25 | 1.25 | 2.5 | 20 | 10 |
| II | C. albicans ATCC 64549 | >200 | 1.5 | 1.5 | >133 | >133 |
| II | C. albicans CCUG 599 | >200 | 1.5 | 1.5 | >133 | >133 |
| II | C. albicans CCUG 1759 | >200 | 1.5 | 1.5 | >133 | >133 |

The results in table 3 show that the peptides according to the invention were much more efficient fungicidal agents than human lactoferrin.

Example 5

In this example an in vitro test was performed to study the anti-inflammatory activity of the peptides according to the invention. More precisely, the inhibitory effect of the peptides according to the invention on the LPS-induced IL-6 response in a monocytic cell line (THP-1) was studied and compared to the effect of human lactoferrin by use of the method described by I. Mattsby-Baltzer et al., Pediatr. Res. 40:257-262, 1996. The IL-6 response in the THP-1 cells was induced by addition of LPS. hLF, peptide 3 and peptide 4, respectively, were added 30 minutes after LPS. A significant inhibition was obtained with peptide 4, as shown in table 3 below. The inhibitory activity of peptide 3 was similar to the inhibitory activity of human lactoferrin.

TABLE 4

| Agent | % inhibition of LPS response |
|---|---|
| hLF | 15 |
| peptide 3 | 17 |
| peptide 4 | 39 |

Example 6

Peptide 3 and peptide 4 according to the invention were also tested in an in vivo study to show their effect on urinary tract infection.

*E. coli* O6K5 was instilled into the urinary bladder of mice. 30 minutes after instillation the different agents specified in table 5 were administered orally in an amount of 500 µg per mouse and 24 hours after instillation the number of bacteria (CFU) present in bladder and in kidney was determined. The result is shown in table 5.

The control group consisted of 10 animals in experiment I and of 23 animals in experiment II. The animals in the control groups were given tap water instead of peptide or hLF.

TABLE 5

| Exp | Agent | Mouse strain | No. of animals | Statistical comparison* of treatment group with control group of the number of bacteria, CFU, present in kidney |
|---|---|---|---|---|
| I | peptide 4 | CH/HeN | 11 | p = 0.0137 |
| II | peptide 3 | C3H/Tif | 23 | p = 0.0574 |
| II | peptide 4 | C3H/Tif | 23 | p = 0.0102 |
| II | hLF | C3H/Tif | 23 | p = 0.006 |

*Mann-Whitney

The results from experiment II are also illustrated in FIG. 1.

Thus, the peptides according to the invention are capable of reducing the number of the bacteria in kidney.

Example 7

In this example an in vitro test was performed to compare the bactericidal and fungicidal activity of the peptides according to the invention with peptides described in EP-A-0 629 347. The peptide according to the invention used was peptide 4, and the peptides according to EP-A-0 629 347 called Morinaga 10, Morinaga 11, Morinaga 12, and Morinaga 13.

The peptides were incubated with $E.\ coli$ O14 and $Candida\ albicans$. Two concentrations of $C.\ albicans$ yeast cells were tested, $5 \cdot 10^6$ and $5 \cdot 10^3$ per ml. Different concentrations of the peptides were tested.

After the incubation, samples were taken for bacterial plating. Serial dilutions of tenfold steps were used in the experiments marked with I in table 5 and of twofold steps in the experiments marked with II.

The concentrations of the different agents required for killing of 100% of the bacteria are given in table 6.

TABLE 6

| | Concentration of agent for 100% killing (µg/ml) | | | |
|---|---|---|---|---|
| | $E.\ coli$ O14 | | $C.\ albicans$ I | |
| Agent | I | II | $5 \cdot 10^6$ | $5 \cdot 10^3$ |
| peptide 4 | >10, <100 | 12 | >10, <100 | 10 |
| hLF | nd | nd | >1000 | >2000 |
| Morinaga 10 | >500 | 1000 | >2000 | >2000 |
| Morinaga 11 | >500 | nd | >2000 | >2000 |
| Morinaga 12 | >500 | nd | >2000 | >2000 |
| Morinaga 13 | >500 | nd | >2000 | >2000 | nd = not determined

From table 6 it is evident that the peptide according to the invention is a much more efficient bactericidal agent than the short peptides described in EP-A-0 629 347 and than human lactoferrin.

Example 8

The fungicidal and inhibitory activity of the peptide 2, peptide 3, peptide 4, and peptide 7 according to the invention were compared to the peptides described in EP-A-0 629 347 most resembling the peptides according to the invention, i.e. Morinaga 24 and Morinaga 25.

$Candida\ albicans$ ATCC 64549 ($1 \cdot 10^5$/ml) was incubated in the presence of the peptides during 2 hours at 37° C. in diluted growth medium (BHI, twofold serial dilutions starting with 50 µg/ml). The fungicidal activity was measured by culturing 5 µl from each incubation well on Saboroud agar plates. The concentrations of the different agents required for killing of 100% of the bacteria is given in table 7.

The inhibition of growth was measured spectrophotometrically after 20 hours of incubation. The concentration of agent needed for inhibition of growth is given in table 7.

TABLE 7

| Agent | Concentration of agent for 100% killing (µg/ml) | Concentration of agent for inhibition of growth (µg/ml) |
|---|---|---|
| Peptide 2 | 6.2 | 6.2 |
| Peptide 3 | 6.2 | 6.2 |
| Peptide 4 | 6.2 | 6.2 |
| Peptide 7 | 3.1 | 1.5 |
| Morinaga 24 | 12.5 | 12.5 |
| Morinaga 25 | 6.2 | 6.2 |

This example show that peptide 2, peptide 3, and peptide 4 according to the invention is more efficient with regard to fungicidal and inhibitory activity than the linear peptide Morinaga 24 and that peptide 7 according to the invention is an even better fungicidal agent and inhibitor of growth of fungi.

Example 9

Also the bactericidal and inhibitory activity of the peptide 2, peptide 3, peptide 4, and peptide 7 according to the invention were compared to the activities of Morinaga 24 and Morinaga 25.

$E.\ coli$ O14 was incubated as described above in the presence of the peptides during 2 hours. The bactericidal activity was measured in the same way as described above. The concentrations of the different agents required for killing of 100% of the bacteria is given in table 8.

The inhibition of growth was measured spectrophotometrically after incubation during 20 hours. The concentration of agent needed for inhibition of growth is given in table 8.

TABLE 8

| Agent | Concentration of agent for 100% killing (µg/ml) | Concentration of agent for inhibition of growth (µg/ml) |
|---|---|---|
| Peptide 2 | 25 | 6.2 |
| Peptide 3 | 12.5 | 3.1 |
| Peptide 4 | 12.5 | 3.1 |
| Peptide 7 | 12.5 | ≦1.5 |
| Morinaga 24 | 25 | 6.2 |
| Morinaga 25 | 12.5 | 3.1 |

This example show that peptide 2, peptide 3 and peptide 4 according to the invention have bactericidal and inhibitory effects that are approximately the same as those for Morinaga 24 and Morinaga 25, but that peptide 7 is much more efficient with regards to inhibition of growth of bacteria.

Example 10

In this example, the microbicidal and microbiostatic activity of the peptides according to the invention were tested and compared to the two reference peptides.

C. albicans (ATCC64549) and E. coli O6, respectively, were incubated with the different peptides. The experiments were performed with 1, 10, 25 and 100 μg/ml of peptide. The results are shown in table 9.

TABLE 9

| Peptide | C. albicans | | E. coli | |
|---|---|---|---|---|
| | MMC$_{99\%}$ | MIC | MMC$_{99\%}$ | MIC |
| Peptide 44 | 10 | 10 | 10 | 10 |
| Peptide 46 | 10 | 10 | 10 | 10 |
| Peptide 48 | 10 | 10 | 10 | 10 |
| Peptide 50 | 10 | 10 | 10 | 10 |
| Peptide 51 | 10 | 10 | 10 | 10 |
| Peptide 53 | 10 | 10 | 10 | 10 |
| Peptide 57 | 25 | 10 | 10 | 10 |
| Peptide 61 | 10 | 10 | 10 | 10 |
| Peptide 63 | 10 | 10 | 10 | 10 |
| Peptide 64 | 25 | 10 | 10 | 10 |
| Peptide 67 | 10 | 10 | 10 | 10 |
| Peptide 40 | 25 | 25 | >25 | >25 |
| Peptide 33 | 100 | 10 | 25 | 10 |

From the table, it is evident that the peptides according to the invention have very good microbicidal and microbiostatic activity, even though the shortest peptide, peptide 40, and the longest peptide, peptide 33, do not give as good results as the other peptides.

Example 11

In this example the activities of the peptides according to the invention on the killing of C. albicans and on the inhibition of the growth of C. albicans were studied.

C. albicans yeast cells (ATCC64549) were incubated for 2 hours at pH 4.5 in BHI medium diluted to 1% of the original concentration containing 25 g/ml of the peptide. Thereafter the fungal solutions were cultured on blood agar plates. OD$_{650}$ was measured after incubation during an additional 18 hours.

The fungicidal effect of the peptides on C. albicans was determined as the ability of the peptide to kill 100% and 99%, respectively, of the fungus, while the growth inhibitory effect was determined by measuring the OD$_{650}$. An inhibitory effect existed when no increase in OD$_{650}$ was recorded. The results are shown in table 10.

TABLE 10

| Peptide | C. albicans | | |
|---|---|---|---|
| | killing: | | |
| | 100% | 99% | inhibition: |
| Peptide 44 | − | − | − |
| Peptide 46 | + | + | + |
| Peptide 48 | + | + | + |

TABLE 10-continued

| Peptide | C. albicans | | |
|---|---|---|---|
| | killing: | | |
| | 100% | 99% | inhibition: |
| Peptide 50 | + | + | + |
| Peptide 51 | + | + | + |
| Peptide 6 | − | + | − |
| Peptide 57 | + | + | + |
| Peptide 61 | − | + | + |
| Peptide 62 | − | + | + |
| Peptide 64 | − | + | + |
| Peptide 66 | − | + | + |
| Peptide 40 | − | − | − |
| Peptide 33 | − | − | − | killing:
+ = 100/99% of the bacteria are killed
− = less than 100/99% of the bacteria are killed
inhibition:
+ = no increase in OD$_{650}$ is seen
− = OD$_{650}$ continues to increase From the table, it is evident that the peptides according to the invention, especially Peptides 46, 48, 50, 51, and 57, have better effect on the killing and growth inhibition of C. albicans than the reference peptides.

Example 12

In this example, the peptides according to the invention were used to study the effect on the killing of different bacteria. The different bacteria used are shown in table 11.

The peptides were used at a concentration of 25 μg/ml.
The results are shown in table 11.

TABLE 11

| Peptide | Bacteria | | | | |
|---|---|---|---|---|---|
| | E. faecalis | S. epidermis | S. aureus | K. pneumoniae | P. aeruginosa |
| Peptide 44 | + | + | + | − | − |
| Peptide 46 | + | + | + | + | + |
| Peptide 48 | + | + | + | + | + |
| Peptide 50 | + | + | + | + | + |
| Peptide 51 | + | + | + | + | + |
| Peptide 6 | + | + | + | + | + |
| Peptide 57 | + | + | + | + | + |
| Peptide 61 | + | + | + | + | + |
| Peptide 62 | + | + | + | + | + |
| Peptide 64 | + | + | + | − | − |
| Peptide 66 | + | + | + | − | − |
| Peptide 40 | − | + | − | − | − |
| Peptide 33 | + | + | + | − | − |

+ = 99% of the bacteria are killed
− = less than 99% of the bacteria are killed

From the table, it is evident that the peptides according to the invention, especially Peptides 46-62, have very good effect on the killing of bacteria, even though the shortest peptide, peptide 40, and the longest peptide, peptide 33, do not give as good results as the other peptides.

Example 13

Figure 2:
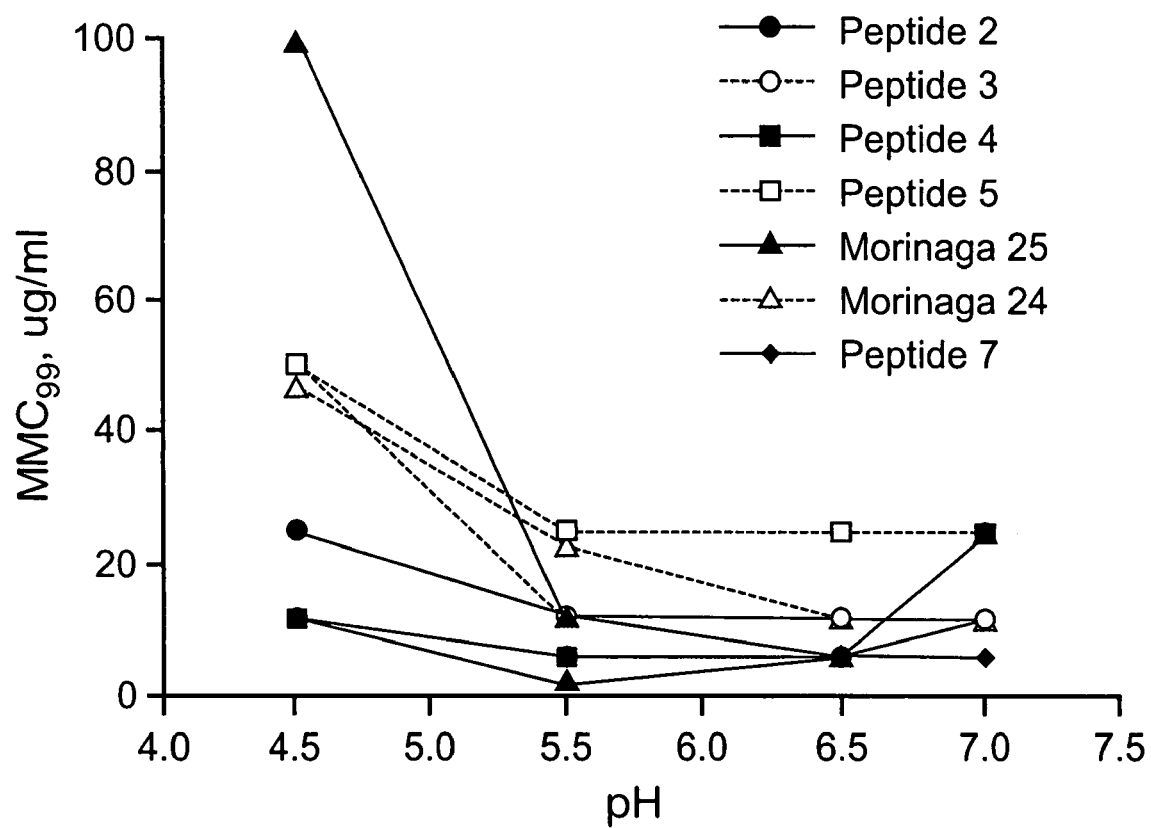
FIG. 2 illustrates the concentrations needed of peptide 3 in linear and cyclic form, peptide 4 in linear and cyclic form, and peptide 7 compared to a reference peptide in linear and cyclic form for killing of 99% of *C. albicans* at different pH.

In this example the concentrations needed of three peptides according to the invention for killing of 99% of C. albicans at different pH was compared to a reference peptide. The peptides according to the invention were peptide 2 (linear), peptide 3 (cyclic), peptide 4 (linear), peptide 5 (cyclic) and peptide 7 (lactam bridged), all capped. The reference peptides used were an uncapped cyclic form and an uncapped linear form of a Morinaga peptide, Morinaga 24 and 25. The results are illustrated in FIG. 2. From the figure it is evident that the capped, linear peptides 3, and 4 as well as the lactam bridge containing peptide 7 have better effects than the capped cyclic peptides according to the invention, and that all the capped linear peptides according to the invention in addition to peptide 7 have better effects than the linear and cyclic, uncapped reference peptides (Morinaga 24 and 25) at pH 4.5. The most effective peptide at all different pH was peptide 7.

Example 14

Figure 3:
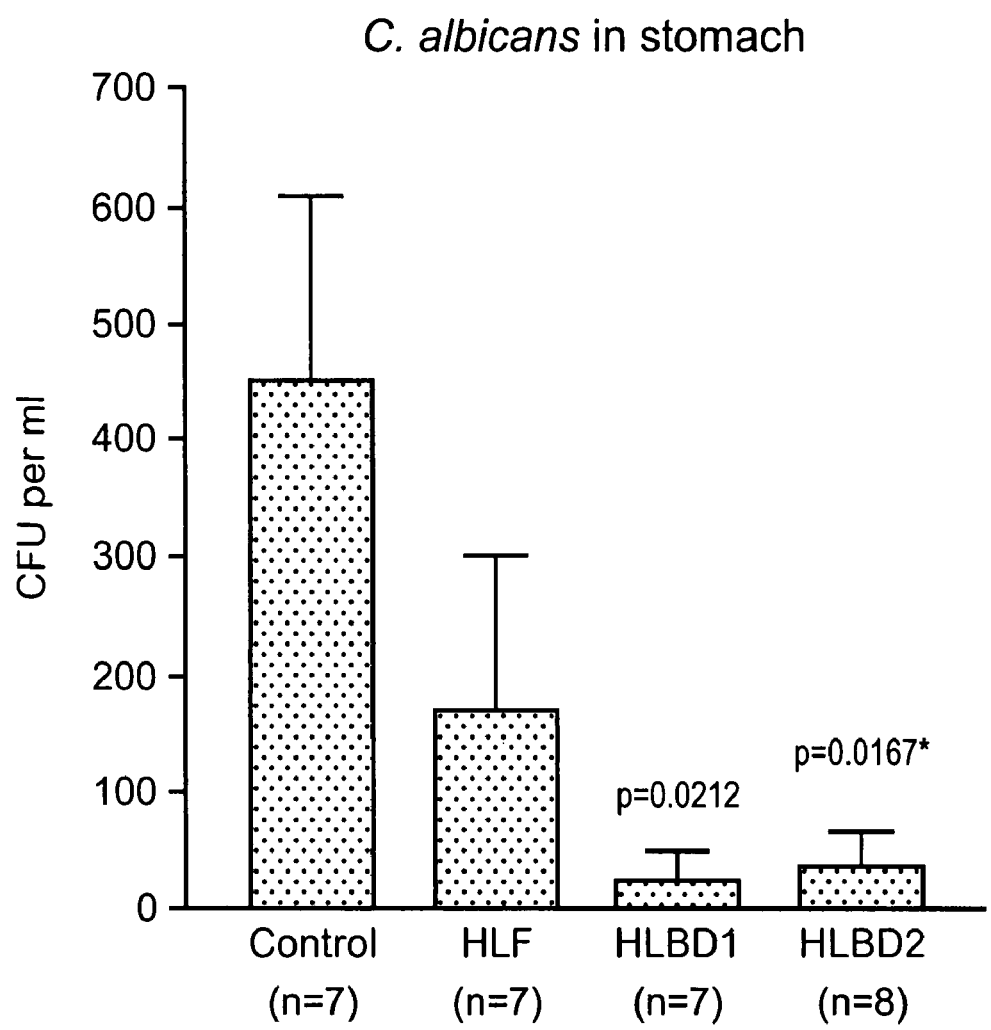
FIG. 3 shows the number of *C. albicans* (CFU) present in stomach in mice, which were orally treated with two peptides according to the invention, peptide 3 and peptide 4, with human lactoferrin (hLF) and with water (Control), respectively, after intragastrical administration of *C. albicans*.

In this example prevention of C. albicans colonisation in stomach was studied by giving human lactoferrin (HFL), the peptide with SEQ. ID. NO. 3 and the peptide with SEQ. ID. NO. 4 perorally to mice. A dose of $10^8$ of C. albicans was given intragstrically to mice. Three days later HLF or peptide was given twice a day (in a total of 1 mg per day) for three days, and on the fourth day the mice were killed. The number of C. albicans in the stomach was determined by culturing and counting colony-forming units (CFU per ml). The results are illustrated in FIG. 3. It is evident from the results that the peptides effectively reduce the growth of C. albicans in the stomach.

Example 15

In this example the anti-inflammatory effects of the peptides according to the invention on experimental colitis in mice were studied. Acute colitis was induced in C57Bl/6J mice by giving dextransulphate (5%) via the drinking water (ad lib). Peptide 3 and peptide 4, as well as human lactoferrin (hLF), were orally administered to mice at the start of dextransulphate treatment. The animals were killed on day 2.

Figure 4A:
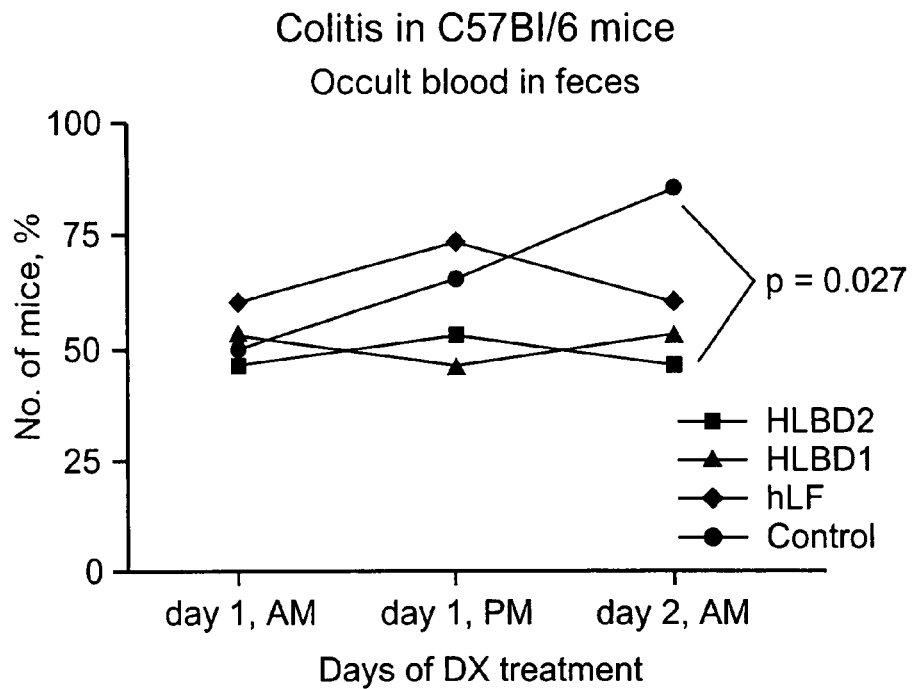
FIG. 4 illustrates the result of peroral treatment of mice with experimental colitis with peptide 3 and peptide 4, and with hLF compared to treatment with water (control). FIG.
FIG. 4B shows the amount of IL-1β in serum.
FIG. 4C shows the occurrence of rectal bleeding.
FIG. 4D shows the colon length.

It was found that blood in faeces of mice treated with the peptides according to the invention occurred in fewer animals than compared to the water-treated control group two days after treatment, as shown in FIG. 4A.

Figure 4B:
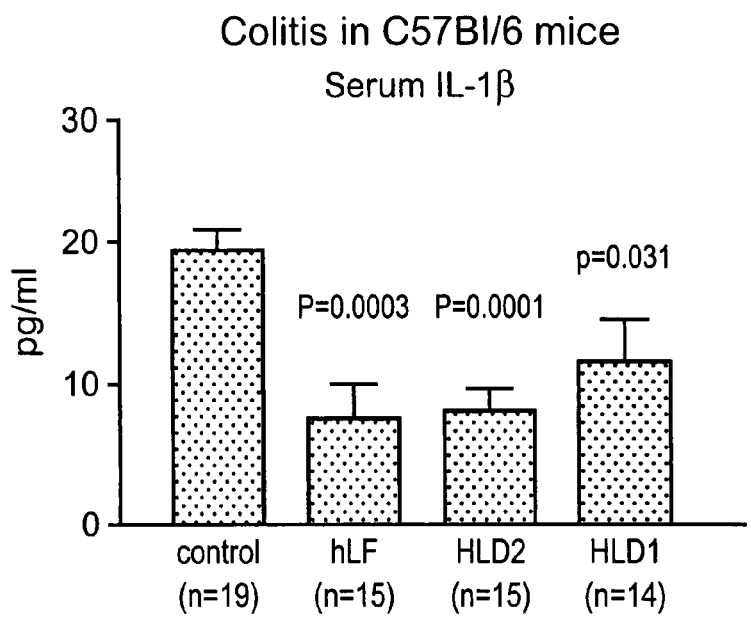
Figure 4C:
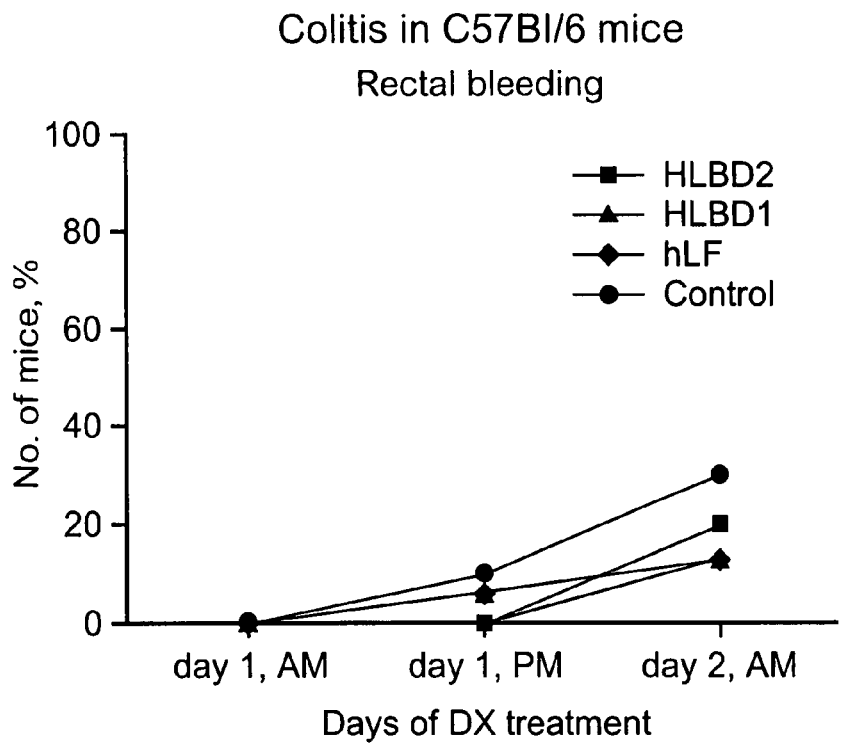

Another indication of the fact that the peptides according to the invention are anti-inflammatory, is the reduced concentrations of the inflammatory cytokine IL-1β present in sera from the mice treated according to the invention, as illustrated in FIG. 4B, as well as the reduced occurrence of rectal bleeding, as shown in FIG. 4C.

Figure 4D:
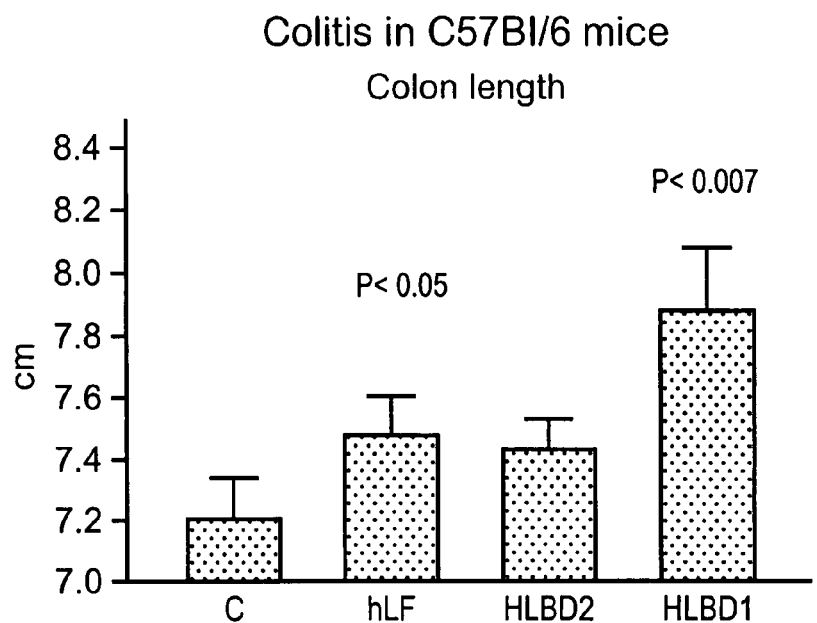

Another measurement of inflammation in the colon is the colon length—a shortened colon is inductive of inflammation. It was found, as shown in FIG. 4D, that the colon of the mice treated according to the invention were longer than the colon of the mice in the control group.

Figure 5A:
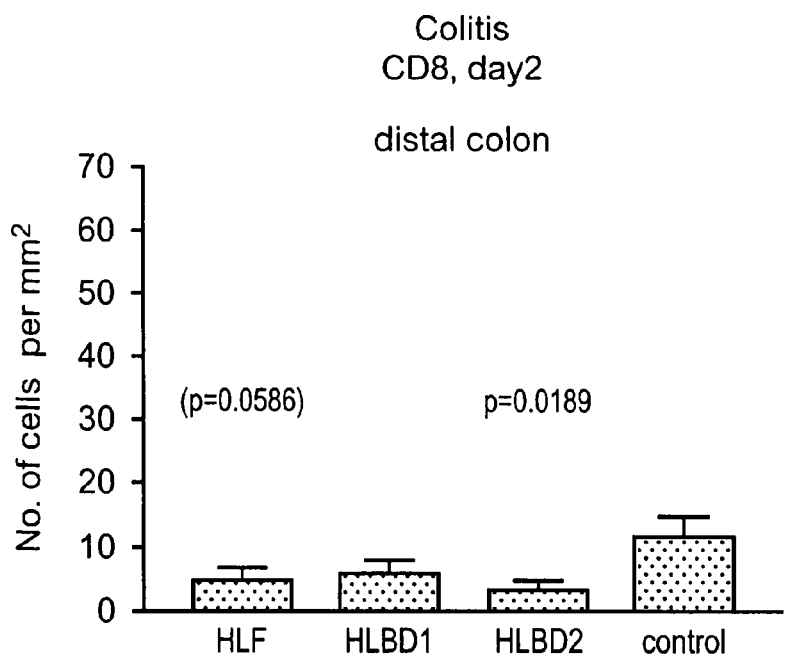
FIG. 5A illustrates the number of CD8 positive cells in tissue sections of distal colon from the mice treated according to FIG. 4.
Figure 5B:
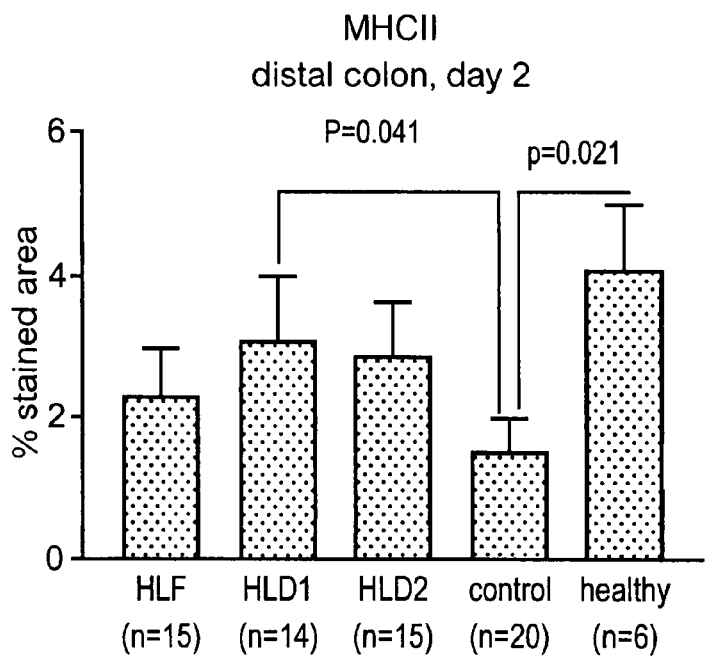
FIG. 5B illustrates the expression of MHC class II in tissue sections of distal colon from the mice treated according to FIG. 4.

Thereafter the number of CD8- and MHC class II-positive cells in tissue sections of distal colon from the mice was studied, and the results are shown in FIG. 5. From FIG. 5A, it is clear that the number of CD8-positive T-cells in tissue sections of distal colon from the mice treated with the peptides according to the invention is significantly lower than for the water-treated control group.

From FIG. 5 it is clear that the occurrence of cells expressing MHC class II (macrophages, dendritic cells and B cells) in tissue sections of distal colon from the mice treated with the peptides according to the invention is higher than for the untreated control group, and similar to that of healthy animals with no acute colitis. These results indicate that mice treated with the peptides according to the invention diminish or delay their local cellular response.

Thus, the peptides according to the invention are effective in reducing the inflammation itself as well as the clinical symptoms.

Example 16

In this example the fungicidal activity of one of the peptides according to the invention, the peptide with SEQ. ID. NO. 7, was compared to the conventional antifungal agents flucytosine and fluconazole, and also to human lactoferrin (hLF). The antifungal agents were tested on C. albicans (ATCC 64549) in a concentration of $2 \times 10^5$ cells/ml. The tests were performed in BHI medium diluted 1/100. The results are shown in table 12.

TABLE 12

| Antifungal agent | MMC$_{99\%}$ (µg/ml) | MIC (µg/ml) |
|---|---|---|
| Flucytosine*⁾ | >500 | 250 |
| Fluconazole | >500 | >500 |
| hLF | >1000 | 1000 |
| Peptide 7 | 6.2 | 6.2 |

*⁾This may be inhibited by nonsynthetic media, however a 1/100 dilution of the medium used herein diminishes this risk.

It is evident from the results in table 12 that the peptide according to the invention is clearly more effective than the other substances.

Example 17

Also in this example one of the peptides according to the invention—this time the peptide with SEQ. ID. NO. 4, was compared to a conventional fungicide, amphotericin. The antifungal activity against C. albicans was studied. Twofold serial dilutions with a starting concentration of 20 µg/ml were used. BHI diluted 1/100 was used as growth medium.

TABLE 13

| Fungicidal agent | MMC$_{99\%}$ (µg/ml) | MIC (µg/ml) |
|---|---|---|
| Peptide 4 | 5.0 | 5.0 |
| Amphotericin | 2.5 | 0.6 |

It is evident from table 13 that the activity of the peptide according to the invention is comparable to the conventional fungicide.

Example 18

In this example the bactericidal activity of two of the peptides according to the invention was studied in a test with a multiresistant S. aureus. A bacterial solution with a concentration of $5.0 \times 10^5$ S. aureus bacterial per ml was used. The concentration of each peptide needed to kill 99% of the bacteria (MMC$_{99}$%) was determined after 2 hours and after 24 hours of incubation at 37° C. The results are illustrated in table 14 below.

TABLE 14

| | MMC$_{99\%}$ (µg/ml) | |
|---|---|---|
| SEQ. ID. NO. | 2 hours | 24 hours |
| 4 | 5.0 | ≦0.32 |
| 48 | 5.0 | ≦0.32 |

Example 19

In this example the bactericidal activity of three of the peptides according to the invention was studied in a test with a reference strain of S. aureus. A bacterial solution with a concentration of $5.0 \times 10^5$ S. aureus bacterial per ml was used. The concentration of each peptide needed to kill 99% of the bacteria ($MMC_{99}\%$) was determined after 2 hours of incubation at 37° C. The lowest concentration tested was 6.25 μg/ml. The results are illustrated in table 15 below.

TABLE 15

| SEQ. ID. NO. | $MMC_{99\%}$ (μg/ml) 2 hours |
|---|---|
| 36 | ≦6.25 |
| 98 | ≦6.25 |
| 7 | ≦6.25 |

Example 20

In this example a so called alanine scan of the peptide with SEQ. ID. NO. 46, C-F-Q-W-Q-R-N-M-R-K-V-R, was performed. In this alanine scan each amino acid was in turn substituted with an alanine, resulting in the peptides illustrated in table 16 below.

TABLE 16

| Exp. | amino acid in position | | | | | | | | | | | | SEQ. |
| No. | 1 | 2 | 3 | 4 | 5 | 6 | 7 | 8 | 9 | 10 | 11 | 12 | ID. NO. |
|---|---|---|---|---|---|---|---|---|---|---|---|---|---|
| 1 | A | F | Q | W | Q | R | N | M | R | K | V | R | 68 |
| 2 | C | A | Q | W | Q | R | N | M | R | K | V | R | 69 |
| 3 | C | F | A | W | Q | R | N | M | R | K | V | R | 70 |
| 4 | C | F | Q | A | Q | R | N | M | R | K | V | R | 71 |
| 5 | C | F | Q | W | A | R | N | M | R | K | V | R | 72 |
| 6 | C | F | Q | W | Q | A | N | M | R | K | V | R | 73 |
| 7 | C | F | Q | W | Q | R | A | M | R | K | V | R | 74 |
| 8 | C | F | Q | W | Q | R | N | A | R | K | V | R | 75 |
| 9 | C | F | Q | W | Q | R | N | M | A | K | V | R | 76 |
| 10 | C | F | Q | W | Q | R | N | M | R | A | V | R | 77 |
| 11 | C | F | Q | W | Q | R | N | M | R | K | A | R | 78 |
| 12 | C | F | Q | W | Q | R | N | M | R | K | V | A | 79 |

Example 21

In each of the experiments in this example one of the amino acids in positions 4, 6, 8 and 9 in the peptide with SEQ. ID. NO. 46 was replaced by a similar amino acid. In experiment 1 the tryptophan in position 4 was replaced by a leucine, in experiment 2 the arginine in position 6 was replaced by a lysine, in experiment 3 the methionine in position 8 was replaced by a leucine, and in experiment 4 the arginine in position 9 was replaced by a lysine. The resulting peptides are illustrated in table 17.

TABLE 17

| Exp. | amino acid in position | | | | | | | | | | | | SEQ. |
| No. | 1 | 2 | 3 | 4 | 5 | 6 | 7 | 8 | 9 | 10 | 11 | 12 | ID. NO. |
|---|---|---|---|---|---|---|---|---|---|---|---|---|---|
| 1 | C | F | Q | L | Q | R | N | M | R | K | V | R | 80 |
| 2 | C | F | Q | W | Q | K | N | M | R | K | V | R | 81 |
| 3 | C | F | Q | W | Q | R | N | L | R | K | V | R | 82 |
| 4 | C | F | Q | W | Q | R | N | M | K | K | V | R | 83 |

Example 22

In each of the experiments in this example one of the amino acids in positions 5, 6, and 7 in the peptide with SEQ. ID. NO. 46 was replaced by a negatively charged amino acid. In experiment 1 the glutamine in position 5 was replaced by a glutamic acid, in experiment 2 the arginine in position 6 was replaced by glutamic acid, and in experiment 3 the asparagine in position 7 was replaced by glutamic acid. The resulting peptides are illustrated in table 18.

TABLE 18

| Exp. | amino acid in position | | | | | | | | | | | | SEQ. |
| No. | 1 | 2 | 3 | 4 | 5 | 6 | 7 | 8 | 9 | 10 | 11 | 12 | ID. NO. |
|---|---|---|---|---|---|---|---|---|---|---|---|---|---|
| 1 | C | F | Q | W | E | R | N | M | R | K | V | R | 84 |
| 2 | C | F | Q | W | Q | E | N | M | R | K | V | R | 85 |
| 3 | C | F | Q | W | Q | R | E | M | R | K | V | R | 86 |

Example 23

In each of the experiments in this example a neutral amino acid in the peptide with SEQ. ID. NO. 46 was replaced with either a positively charged amino acid or a neutral-one. In experiment 1 the glutamine in position 5 was replaced by an ornithine, in experiment 2 the glutamine in position 5 was replaced by a norleucine, in experiment 3 the asparagine in position 7 was replaced by an ornithine, and in experiment 4 the asparagine in position 7 was replaced by a norleucine. The resulting peptides are illustrated in table 19.

TABLE 19

| Exp. | amino acid in position | | | | | | | | | | | | SEQ. |
| No. | 1 | 2 | 3 | 4 | 5 | 6 | 7 | 8 | 9 | 10 | 11 | 12 | ID. NO. |
|---|---|---|---|---|---|---|---|---|---|---|---|---|---|
| 1 | C | F | Q | W | Orn | R | N | M | R | K | V | R | 87 |
| 2 | C | F | Q | W | Nle | R | N | M | R | K | V | R | 88 |
| 3 | C | F | Q | W | Q | R | Orn | M | R | K | V | R | 89 |
| 4 | C | F | Q | W | Q | R | Nle | M | R | K | V | R | 90 |

Example 24

In each of the experiments in this example one or several of the amino acids in the peptide with SEQ. ID. NO. 46 was replaced with other amino acids. In experiment 1 the glutamine in position 5 was replaced with a lysine, in experiment 2 the glutamine in position 5 was replaced with an lysine and the asparagine in position 7 was replaced by an alanine, in experiment 3 the glutamine in position 3 was replaced with an alanine and the glutamine in position 5 was replaced with an lysine, in experiment 4 the glutamine in position 3 and the asparagine in position 7 were replaced with alanines, in experiment 5 the tryptophan in position 4 was replaced with a leucine, and the arginines in position 6 and position 9 were replaced with lysines, and in experiment 6 the glutamine in position 3 and the asparagine in position 7 were replaced with alanine, the tryptophan in position 4 was replaced with a leucine, and the glutamine in position 5 and the arginines in positions 6 and 9 were replaced with lysines. The resulting peptides are illustrated in table 20.

TABLE 20

| Exp. | amino acid in position | | | | | | | | | | | | SEQ. |
| --- | --- | --- | --- | --- | --- | --- | --- | --- | --- | --- | --- | --- | --- |
| No. | 1 | 2 | 3 | 4 | 5 | 6 | 7 | 8 | 9 | 10 | 11 | 12 | ID. NO. |
| 1 | C | F | Q | W | K | R | N | M | R | K | V | R | 91 |
| 2 | C | F | Q | W | K | R | A | M | R | K | V | R | 92 |
| 3 | C | F | A | W | K | R | N | M | R | K | V | R | 93 |
| 4 | C | F | A | W | Q | R | A | M | R | K | V | R | 94 |
| 5 | C | F | Q | L | Q | K | N | M | K | K | V | R | 95 |
| 6 | C | F | A | L | K | K | A | M | K | K | V | R | 96 |

Example 25

In this example the fungicidal, and bactericidal effects of the different peptides obtained in examples 18-21 were studied. *C. albicans*, *E. coli* and *S. aureus*, respectively, were incubated in BHI medium diluted 1/100, with a pH of approximately 6.7-6.9. The concentration of each peptide needed to kill 99% of the microorganisms ($MMC_{99\%}$) was determined. The results are illustrated in table 21 below.

TABLE 21

| | $MMC_{99\%}$ | | |
| --- | --- | --- | --- |
| SEQ. ID. NO. | C. albicans | E. coli | S. aureus |
| 46 | 12 | 12 | 7 |
| 68 | 12 | >25 | 28 |
| 69 | 12 | 12 | 14 |
| 70 | 6 | 6 | 7 |
| 71 | 12 | 25 | 14 |
| 72 | 12 | 12 | 7 |
| 73 | 12 | 12 | 7 |
| 74 | 6 | 6 | 3.5 |
| 75 | 25 | 12 | 7 |
| 76 | 25 | 25 | 7 |
| 77 | 25 | 12 | 7 |
| 78 | 25 | 12 | 7 |
| 79 | 25 | 12 | 7 |
| 80 | 6 | 12 | 7 |
| 81 | 6 | 6 | 7 |
| 82 | 6 | 12 | 7 |
| 83 | 6 | 6 | 7 |
| 84 | 12 | 25 | 14 |
| 85 | >50 | >25 | >28 |
| 86 | 25 | 25 | 14 |
| 87 | 3 | 6 | ≦3.5 |
| 88 | 6 | 12 | 3.5 |
| 89 | 6 | 6 | 3.5 |
| 90 | 12 | 12 | 3.5 |

Example 26

In this example the fungicidal, and bactericidal effects of the different peptides obtained in example 22 were studied. *C. albicans*, *E. coli* and *S. aureus*, respectively, were incubated in BHI medium diluted 1/100, with a pH of approximately 6.7-6.9. The concentration of each peptide needed to kill 99% of the microorganisms ($MMC_{99\%}$) was determined. The results are illustrated in table 22 below.

TABLE 22

| | $MMC_{99\%}$ | | |
| --- | --- | --- | --- |
| SEQ. ID. NO. | C. albicans | E. coli | S. aureus |
| 46 | 12 | 6 | 12 |
| 91*) | 6 | 6 | 6 |
| 93 | 12 | 6 | 6 |
| 94 | 12 | 6 | 6 |
| 95 | 12 | 6 | 6 |
| 96 | 12 | 6 | 12 |
| 97 | 12 | 6 | 6 |

*)The peptide with SEQ. ID. NO. 91 was tested twice, and the results were the same at both times.

Example 27

In this example the fungicidal activity of three of the peptides according to the invention was studied, and tested against three different fungi. The fungi were incubated in BHI medium diluted 1/100. The concentration of each peptide needed to kill 99% of the fungi ($MMC_{99\%}$) was determined. The results are illustrated in table 23 below.

TABLE 23

| | $MMC_{99\%}$ | | |
| --- | --- | --- | --- |
| SEQ. ID. NO. | C. albicans | C. glabrata | C. neoformans |
| 4 | 6.3 | >50 | ≦3.1 |
| 46 | 12.5 | 50 | ND |
| 87 | 6.3 | >50 | 3.1 |

Example 28

In this example the microbicidal activity of eight of the peptides according to the invention was studied, and tested against *E. coli* O6K5 and *C. albicans*.

In this example, a peptide with SEQ. ID. NO. 55 was used, which has not been described above. This peptide is a modification of the peptide with SEQ. ID. NO. 7 wherein the Asp in position 9 is substituted with a Glu.

The concentration of each peptide needed to kill 99% of the microorganisms ($MMC_{99\%}$) was determined. The results are illustrated in table 24 below.

TABLE 24

| | $MMC_{99\%}$ | |
| --- | --- | --- |
| SEQ. ID. NO. | E. coli | C. albicans |
| 4 | 20 | 5 |
| 7 | >20 | 5 |
| 55 | 5 | 5 |
| 46 | 10 | 10 |
| 87 | 5 | 5 |
| 88 | 5 | 10 |
| 91 | 5 | 5 |
| 93 | 5 | 5 |

The conclusion of the results of tables 21-24 is that the peptide sequence can be modified at several positions and by that increase or keep the microbicidal activity compared with the natural sequence. These modified sequences also reduce the costs for synthesis of the peptides. The positions at which amino acids can be changed with better or equal results are the ones denoted Xaa in SEQ. ID. NO. 99.

The invention claimed is:

1. A purified peptide comprising Phe-$X_1$-Trp-$X_2$-Arg-$X_3$-Met-Arg-Lys-$X_4$-Arg (SEQ ID NO:43) wherein $X_1$, $X_2$, $X_3$, and $X_4$ are, independently of each other, Gln, Lys, Asp, Asn, or Val, and wherein the peptide is selected from the group consisting of SEQ ID NOS:6, 7, 52-61 and 98.

2. The purified peptide of claim 1, wherein the peptide is SEQ ID NO: 7, 53, 55, 57, 61, or 98.

3. The purified peptide of claim 2, wherein the peptide is SEQ ID NO: 7.

4. A medicinal product comprising a peptide of claim 1.

5. The medicinal product of claim 4 formulated for oral administration.

6. The medicinal product of claim 4 formulated for parenteral administration.

7. The medicinal product of claim 4 formulated for topical administration.

8. The medicinal product of claim 7 formulated for administration on mucosal membranes.

9. A food stuff comprising a peptide of claim 1.

10. The food stuff of claim 9, wherein the food stuff is an infant formula food.

11. A method of treating infections or inflammations comprising administering to a patient in need thereof an amount of a peptide of claim 1, wherein the amount of peptide is effective to reduce infections or inflammations.

12. The method of claim 11, wherein the infection is a urinary tract infection.

13. The method of claim 11, wherein the inflammation or infection is colitis.

14. The method of claim 11, wherein the infection is a candida infection on a mucosal membrane.

15. The method of claim 11, wherein the peptide is administered orally.

16. The method of claim 15, wherein the peptide is administered orally in a food stuff.

17. The method of claim 16, wherein food stuff is an infant formula food.

18. The method of claim 11, wherein the peptide is administered parenterally.

19. The method of claim 11, wherein the peptide is administered topically.

20. The method of claim 19, wherein the peptide is administered on mucosal membranes.

* * * * *

SEQUENCE LISTING

<160> NUMBER OF SEQ ID NOS: 102

<210> SEQ ID NO 1
<211> LENGTH: 25
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: PEPTIDE
<222> LOCATION: (1)
<223> OTHER INFORMATION: Amino acid 1 is Xaa wherein Xaa = Glu or no
      amino acid.
<220> FEATURE:
<221> NAME/KEY: PEPTIDE
<222> LOCATION: (2)
<223> OTHER INFORMATION: Amino acid 2 is Xaa wherein Xaa = Ala or no
      amino acid.
<220> FEATURE:
<221> NAME/KEY: PEPTIDE
<222> LOCATION: (5)
<223> OTHER INFORMATION: Amino acid 5 is Xaa wherein Xaa = Cys or Ala.
<220> FEATURE:
<221> NAME/KEY: PEPTIDE
<222> LOCATION: (7)
<223> OTHER INFORMATION: Amino acid 7 is Xaa wherein Xaa = Gln or Lys.
<220> FEATURE:
<221> NAME/KEY: PEPTIDE
<222> LOCATION: (11)
<223> OTHER INFORMATION: Amino acid 11 is Xaa wherein Xaa = Asn or Asp.
<220> FEATURE:
<221> NAME/KEY: PEPTIDE
<222> LOCATION: (17)..(25)
<223> OTHER INFORMATION: Amino acids 17-25 are Xaa wherein Xaa = Gly,
      Pro, Pro, Val, Ser, Cys, Ile, Lys, Arg
<220> FEATURE:
<221> NAME/KEY: MOD_RES
<222> LOCATION: (25)
<223> OTHER INFORMATION: AMIDATION
<220> FEATURE:
<223> OTHER INFORMATION: Description of Artificial Sequence: of natural
      or artificial origin, corresponding to modification of the
      sequence consisting of aa 16-40 in human lactoferrin

<400> SEQUENCE: 1

Xaa Xaa Thr Lys Xaa Phe Xaa Trp Gln Arg Xaa Met Arg Lys Val Arg
 1               5                  10                  15

Xaa Xaa Xaa Xaa Xaa Xaa Xaa Xaa Xaa
            20                  25

<210> SEQ ID NO 2
<211> LENGTH: 25
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (25)
<223> OTHER INFORMATION: AMIDATION
<220> FEATURE:
<223> OTHER INFORMATION: Description of Artificial Sequence: of natural
      or artificial origin, corresponding to a modification
      of the sequence consisting of amino acids 16-40 in
      human lactoferrin

<400> SEQUENCE: 2

Glu Ala Thr Lys Cys Phe Gln Trp Gln Arg Asn Met Arg Lys Val Arg

```
                1               5                   10                  15
Gly Pro Pro Val Ser Cys Ile Lys Arg
                20                  25

<210> SEQ ID NO 3
<211> LENGTH: 25
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (25)
<223> OTHER INFORMATION: AMIDATION
<220> FEATURE:
<221> NAME/KEY: DISULFID
<222> LOCATION: (5)..(22)
<220> FEATURE:
<223> OTHER INFORMATION: Description of Artificial Sequence: of natural
      or artificial origin, corresponding to a modification
      of the sequence consisting of amino acids 16-40 in
      human lactoferrin

<400> SEQUENCE: 3

Glu Ala Thr Lys Cys Phe Gln Trp Gln Arg Asn Met Arg Lys Val Arg
 1               5                   10                  15

Gly Pro Pro Val Ser Cys Ile Lys Arg
                20                  25

<210> SEQ ID NO 4
<211> LENGTH: 23
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (23)..(23)
<223> OTHER INFORMATION: AMIDATION
<220> FEATURE:
<223> OTHER INFORMATION: Description of Artificial Sequence: of natural
      or artificial origin, corresponding to a modification
      of the sequence consisting of amino acids 18-40 in
      human lactoferrin

<400> SEQUENCE: 4

Thr Lys Cys Phe Gln Trp Gln Arg Asn Met Arg Lys Val Arg Gly Pro
 1               5                   10                  15

Pro Val Ser Cys Ile Lys Arg
                20

<210> SEQ ID NO 5
<211> LENGTH: 23
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (23)
<223> OTHER INFORMATION: AMIDATION
<220> FEATURE:
<221> NAME/KEY: DISULFID
<222> LOCATION: (3)..(20)
<220> FEATURE:
```

```
<223> OTHER INFORMATION: Description of Artificial Sequence: of natural
      or artificial origin, corresponding to a modification
      of the sequence consisting of amino acids 18-40 in
      human lactoferrin

<400> SEQUENCE: 5

Thr Lys Cys Phe Gln Trp Gln Arg Asn Met Arg Lys Val Arg Gly Pro
 1               5                  10                  15

Pro Val Ser Cys Ile Lys Arg
            20

<210> SEQ ID NO 6
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<223> OTHER INFORMATION: Description of Artificial Sequence: of natural
      or artificial origin, corresponding to a modification
      of the sequence consisting of amino acids 18-31 in
      human lactoferrin

<400> SEQUENCE: 6

Thr Lys Ala Phe Lys Trp Gln Arg Asp Met Arg Lys Val Arg
 1               5                  10

<210> SEQ ID NO 7
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<221> NAME/KEY: BINDING
<222> LOCATION: (5)..(9)
<223> OTHER INFORMATION: LACTAM
<220> FEATURE:
<223> OTHER INFORMATION: Description of Artificial Sequence: of natural
      or artificial origin, corresponding to a modification
      of the sequence consisting of aa 18-31 in human
      lactoferrin; a lactam is formed between aa 5 and 9

<400> SEQUENCE: 7

Thr Lys Ala Phe Lys Trp Gln Arg Asp Met Arg Lys Val Arg
 1               5                  10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 12-31 of the protein
      human lactoferrin

<400> SEQUENCE: 8

Val Ser Gln Pro Glu Ala Thr Lys Cys Phe Gln Trp Gln Arg Asn Met
```

```
                1               5              10              15
Arg Lys Val Arg
            20

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 12-18 of the protein
      human lactoferrin

<400> SEQUENCE: 9

Val Ser Gln Pro Glu Ala Thr
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 13-19 of the protein
      human lactoferrin

<400> SEQUENCE: 10

Ser Gln Pro Glu Ala Thr Lys
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 14-20 of the protein
      human lactoferrin

<400> SEQUENCE: 11

Gln Pro Glu Ala Thr Lys Cys
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 15-21 of the protein
      human lactoferrin

<400> SEQUENCE: 12

Pro Glu Ala Thr Lys Cys Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-22 of the protein
      human lactoferrin
```

```
<400> SEQUENCE: 13

Glu Ala Thr Lys Cys Phe Gln
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 17-23 of the protein
      human lactoferrin

<400> SEQUENCE: 14

Ala Thr Lys Cys Phe Gln Trp
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 18-24 of the protein
      human lactoferrin

<400> SEQUENCE: 15

Thr Lys Cys Phe Gln Trp Gln
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 19-25 of the protein
      human lactoferrin

<400> SEQUENCE: 16

Lys Cys Phe Gln Trp Gln Arg
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 20-26 of the protein
      human lactoferrin

<400> SEQUENCE: 17

Cys Phe Gln Trp Gln Arg Asn
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 21-27 of the protein
``` human lactoferrin

<400> SEQUENCE: 18

Phe Gln Trp Gln Arg Asn Met
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 22-28 of the protein
      human lactoferrin

<400> SEQUENCE: 19

Gln Trp Gln Arg Asn Met Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 23-29 of the protein
      human lactoferrin

<400> SEQUENCE: 20

Trp Gln Arg Asn Met Arg Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 24-30 of the protein
      human lactoferrin

<400> SEQUENCE: 21

Gln Arg Asn Met Arg Lys Val
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 25-31 of the protein
      human lactoferrin

<400> SEQUENCE: 22

Arg Asn Met Arg Lys Val Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Peptide of
      natural or artificial origin consisting of the

```
        amino acids in positions 16-23 of the protein
        human lactoferrin

<400> SEQUENCE: 23

Glu Ala Thr Lys Cys Phe Gln Trp
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-24 of the protein
      human lactoferrin

<400> SEQUENCE: 24

Glu Ala Thr Lys Cys Phe Gln Trp Gln
  1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-25 of the protein
      human lactoferrin

<400> SEQUENCE: 25

Glu Ala Thr Lys Cys Phe Gln Trp Gln Arg
  1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-26 of the protein
      human lactoferrin

<400> SEQUENCE: 26

Glu Ala Thr Lys Cys Phe Gln Trp Gln Arg Asn
  1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-27 of the protein
      human lactoferrin

<400> SEQUENCE: 27

Glu Ala Thr Lys Cys Phe Gln Trp Gln Arg Asn Met
  1               5                  10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Peptide of
``` natural or artificial origin consisting of the
amino acids in positions 16-28 of the protein
human lactoferrin

<400> SEQUENCE: 28

Glu Ala Thr Lys Cys Phe Gln Trp Gln Arg Asn Met Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-29 of the protein
      human lactoferrin

<400> SEQUENCE: 29

Glu Ala Thr Lys Cys Phe Gln Trp Gln Arg Asn Met Arg Lys
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-30 of the protein
      human lactoferrin

<400> SEQUENCE: 30

Glu Ala Thr Lys Cys Phe Gln Trp Gln Arg Asn Met Arg Lys Val
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16-31 of the protein
      human lactoferrin

<400> SEQUENCE: 31

Glu Ala Thr Lys Cys Phe Gln Trp Gln Arg Asn Met Arg Lys Val Arg
1               5                   10                  15

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 13-31 of the protein
      human lactoferrin

<400> SEQUENCE: 32

Ser Gln Pro Glu Ala Thr Lys Cys Phe Gln Trp Gln Arg Asn Met Arg
1               5                   10                  15

Lys Val Arg

<210> SEQ ID NO 33
<211> LENGTH: 18
<212> TYPE: PRT

```
<213> ORGANISM: Artificial Sequence
<220> FEATURE:
<223> OTHER INFORMATION: Description of Artificial Sequence: Peptide of
      natural or artificial origin consisting of the
      amino acids in positions 14-31 of the protein
      human lactoferrin

<400> SEQUENCE: 33

Gln Pro Glu Ala Thr Lys Cys Phe Gln Trp Gln Arg Asn Met Arg Lys
 1               5                  10                  15
Val Arg

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 15-31 of the protein
      human lactoferrin

<400> SEQUENCE: 34

Pro Glu Ala Thr Lys Cys Phe Gln Trp Gln Arg Asn Met Arg Lys Val
 1               5                  10                  15
Arg

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 17-31 of the protein
      human lactoferrin

<400> SEQUENCE: 35

Ala Thr Lys Cys Phe Gln Trp Gln Arg Asn Met Arg Lys Val Arg
 1               5                  10                  15

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 18-31 of the protein
      human lactoferrin

<400> SEQUENCE: 36

Thr Lys Cys Phe Gln Trp Gln Arg Asn Met Arg Lys Val Arg
 1               5                  10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 19-31 of the protein
      human lactoferrin

<400> SEQUENCE: 37

Lys Cys Phe Gln Trp Gln Arg Asn Met Arg Lys Val Arg
 1               5                  10
```

```
<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 20-31 of the protein
      human lactoferrin

<400> SEQUENCE: 38

Cys Phe Gln Trp Gln Arg Asn Met Arg Lys Val Arg
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 21-31 of the protein
      human lactoferrin

<400> SEQUENCE: 39

Phe Gln Trp Gln Arg Asn Met Arg Lys Val Arg
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 22-31 of the protein
      human lactoferrin

<400> SEQUENCE: 40

Gln Trp Gln Arg Asn Met Arg Lys Val Arg
 1               5                  10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 23-31 of the protein
      human lactoferrin

<400> SEQUENCE: 41

Trp Gln Arg Asn Met Arg Lys Val Arg
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 24-31 of the protein
      human lactoferrin

<400> SEQUENCE: 42

Gln Arg Asn Met Arg Lys Val Arg
```

```
                              1               5

<210> SEQ ID NO 43
<211> LENGTH: 11
<212> TYPE: PRT
<213> ORGANISM: Artificial Sequence
<220> FEATURE:
<221> NAME/KEY: PEPTIDE
<222> LOCATION: (2)..(10)
<223> OTHER INFORMATION: Amino acids 2, 4, 6 and 10 are Xaa wherein
      Xaa = Gln, Lys, Asp, Asn or Val.
<220> FEATURE:
<223> OTHER INFORMATION: Description of Artificial Sequence: of natural
      or artificial origin, corresponding to a modification
      of the sequence consisting of amino acids 21-31 in
      human lactoferrin

<400> SEQUENCE: 43

Phe Xaa Trp Xaa Arg Xaa Met Arg Lys Xaa Arg
  1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: of natural
      or artificial origin, corresponding to  the sequence
      consisting of amino acids 21-31 in human
      lactoferrin

<400> SEQUENCE: 44

Phe Gln Trp Gln Arg Asn Met Arg Lys Val Arg
  1               5                  10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 21-31 in human lactoferrin
      wherein one aa has been substituted

<400> SEQUENCE: 45

Phe Gln Trp Gln Arg Asn Met Arg Lys Val Arg
  1               5                  10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 46

Cys Phe Gln Trp Gln Arg Asn Met Arg Lys Val Arg
  1               5                  10

<210> SEQ ID NO 47
<211> LENGTH: 12
<212> TYPE: PRT
<213> ORGANISM: Artificial Sequence
<220> FEATURE:
<221> NAME/KEY: MOD_RES
<222> LOCATION: (1)
```

```
<223> OTHER INFORMATION: ACETYLATION
<220> FEATURE:
<221> NAME/KEY: MOD_RES
<222> LOCATION: (12)
<223> OTHER INFORMATION: AMIDATION
<220> FEATURE:
<223> OTHER INFORMATION: Description of Artificial Sequence: of natural
      or artificial origin, corresponding to the sequence
      consisting of aa 20-31 in human lactoferrin

<400> SEQUENCE: 47

Cys Phe Gln Trp Gln Arg Asn Met Arg Lys Val Arg
 1               5                  10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 19-31 in human lactoferrin

<400> SEQUENCE: 48

Lys Cys Phe Gln Trp Gln Arg Asn Met Arg Lys Val Arg
 1               5                  10

<210> SEQ ID NO 49
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (13)
<223> OTHER INFORMATION: AMIDATION
<220> FEATURE:
<223> OTHER INFORMATION: Description of Artificial Sequence: of natural
      or artificial origin, corresponding to the sequence
      consisting of aa 19-31 in human lactoferrin
      wherein one aa has been modified

<400> SEQUENCE: 49

Lys Cys Phe Gln Trp Gln Arg Asn Met Arg Lys Val Arg
 1               5                  10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 18-31 in human lactoferrin

<400> SEQUENCE: 50

Thr Lys Cys Phe Gln Trp Gln Arg Asn Met Arg Lys Val Arg
 1               5                  10

<210> SEQ ID NO 51
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
```

```
<221> NAME/KEY: MOD_RES
<222> LOCATION: (14)
<223> OTHER INFORMATION: AMIDATION
<220> FEATURE:
<223> OTHER INFORMATION: Description of Artificial Sequence: of natural
      or artificial origin, corresponding to the sequence
      consisting of aa 18-31 in human lactoferrin

<400> SEQUENCE: 51

Thr Lys Cys Phe Gln Trp Gln Arg Asn Met Arg Lys Val Arg
  1               5                  10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18-31 in
      human lactoferrin

<400> SEQUENCE: 52

Thr Lys Ala Phe Lys Trp Gln Arg Asp Met Arg Lys Val Arg
  1               5                  10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18-31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 53

Thr Lys Ala Phe Lys Trp Gln Arg Glu Met Arg Lys Val Arg
  1               5                  10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of aa 18-31 in human
      lactoferrin; a lactam is formed between aa 5 and 9
<220> FEATURE:
<221> NAME/KEY: BINDING
<222> LOCATION: (5)..(9)
<223> OTHER INFORMATION: LACTAM

<400> SEQUENCE: 54

Thr Lys Ala Phe Lys Trp Gln Arg Asp Met Arg Lys Val Arg
  1               5                  10

<210> SEQ ID NO 55
<211> LENGTH: 14
<212> TYPE: PRT
<213> ORGANISM: Artificial Sequence
<220> FEATURE:
```

```
<223> OTHER INFORMATION: Description of Artificial Sequence: of natural
      or artificial origin, corresponding to a modification
      of the sequence consisting of aa 18-31 in human
      lactoferrin; a lactam is formed between aa 5 and 9
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<221> NAME/KEY: BINDING
<222> LOCATION: (5)..(9)
<223> OTHER INFORMATION: LACTAM

<400> SEQUENCE: 55

Thr Lys Ala Phe Lys Trp Gln Arg Glu Met Arg Lys Val Arg
  1               5                  10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18-31 in
      human lactoferrin

<400> SEQUENCE: 56

Thr Lys Lys Phe Gln Trp Gln Arg Asn Met Arg Lys Val Arg
  1               5                  10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18-31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 57

Thr Lys Lys Phe Gln Trp Gln Arg Asn Met Arg Lys Val Arg
  1               5                  10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18-31 in
      human lactoferrin

<400> SEQUENCE: 58

Thr Lys Lys Phe Gln Trp Asp Arg Lys Met Arg Lys Asp Arg
  1               5                  10
```

```
<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18-31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 59

Thr Lys Lys Phe Gln Trp Asp Arg Lys Met Arg Lys Asp Arg
 1               5                  10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresp. to a modification of the seq.
      consisting of aa 18-31 in human lactoferrin; lactams formed
      between aa 3 and 7, and 9 and 13
<220> FEATURE:
<221> NAME/KEY: BINDING
<222> LOCATION: (3)..(7)
<223> OTHER INFORMATION: LACTAM
<220> FEATURE:
<221> NAME/KEY: BINDING
<222> LOCATION: (9)..(13)
<223> OTHER INFORMATION: LACTAM

<400> SEQUENCE: 60

Thr Lys Lys Phe Gln Trp Asp Arg Lys Met Arg Lys Asp Arg
 1               5                  10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresp. to a modification of the seq.
      consisting of aa 18-31 in human lactoferrin; lactams formed
      between aa 3 and 7, and 9 and 13
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<221> NAME/KEY: BINDING
<222> LOCATION: (3)..(7)
<223> OTHER INFORMATION: LACTAM
<220> FEATURE:
<221> NAME/KEY: BINDING
<222> LOCATION: (9)..(13)
<223> OTHER INFORMATION: LACTAM

<400> SEQUENCE: 61

Thr Lys Lys Phe Gln Trp Asp Arg Lys Met Arg Lys Asp Arg
 1               5                  10
```

```
<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of amino acids 17-31 in human
      lactoferrin

<400> SEQUENCE: 62

Ala Thr Lys Cys Phe Gln Trp Gln Arg Asn Met Arg Lys Val Arg
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 17-31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (15)
<223> OTHER INFORMATION: AMIDATION

<400> SEQUENCE: 63

Ala Thr Lys Cys Phe Gln Trp Gln Arg Asn Met Arg Lys Val Arg
 1               5                  10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of amino acids 16-31 in human
      lactoferrin

<400> SEQUENCE: 64

Glu Ala Thr Lys Cys Phe Gln Trp Gln Arg Asn Met Arg Lys Val Arg
 1               5                  10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 16-31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (16)
<223> OTHER INFORMATION: AMIDATION

<400> SEQUENCE: 65

Glu Ala Thr Lys Cys Phe Gln Trp Gln Arg Asn Met Arg Lys Val Arg
 1               5                  10                  15
```

```
<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of amino acids 15-31 in human
      lactoferrin

<400> SEQUENCE: 66

Pro Glu Ala Thr Lys Cys Phe Gln Trp Gln Arg Asn Met Arg Lys Val
 1               5                  10                  15

Arg

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 15-31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (17)
<223> OTHER INFORMATION: AMIDATION

<400> SEQUENCE: 67

Pro Glu Ala Thr Lys Cys Phe Gln Trp Gln Arg Asn Met Arg Lys Val
 1               5                  10                  15

Arg

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 68

Ala Phe Gln Trp Gln Arg Asn Met Arg Lys Val Arg
 1               5                  10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 69

Cys Ala Gln Trp Gln Arg Asn Met Arg Lys Val Arg
 1               5                  10

<210> SEQ ID NO 70
```

-continued

```
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 70

Cys Phe Ala Trp Gln Arg Asn Met Arg Lys Val Arg
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 71

Cys Phe Gln Ala Gln Arg Asn Met Arg Lys Val Arg
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 72

Cys Phe Gln Trp Ala Arg Asn Met Arg Lys Val Arg
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been modified

<400> SEQUENCE: 73

Cys Phe Gln Trp Gln Ala Asn Met Arg Lys Val Arg
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 74

Cys Phe Gln Trp Gln Arg Ala Met Arg Lys Val Arg
 1               5                  10
```

```
<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 75

Cys Phe Gln Trp Gln Arg Asn Ala Arg Lys Val Arg
  1               5                  10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 76

Cys Phe Gln Trp Gln Arg Asn Met Ala Lys Val Arg
  1               5                  10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 77

Cys Phe Gln Trp Gln Arg Asn Met Arg Ala Val Arg
  1               5                  10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 78

Cys Phe Gln Trp Gln Arg Asn Met Arg Lys Ala Arg
  1               5                  10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 79

Cys Phe Gln Trp Gln Arg Asn Met Arg Lys Val Ala
  1               5                  10
```

```
<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 80

Cys Phe Gln Leu Gln Arg Asn Met Arg Lys Val Arg
  1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 81

Cys Phe Gln Trp Gln Lys Asn Met Arg Lys Val Arg
  1               5                  10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 82

Cys Phe Gln Trp Gln Arg Asn Leu Arg Lys Val Arg
  1               5                  10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 83

Cys Phe Gln Trp Gln Arg Asn Met Lys Lys Val Arg
  1               5                  10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 84

Cys Phe Gln Trp Glu Arg Asn Met Arg Lys Val Arg
  1               5                  10
```

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 85

Cys Phe Gln Trp Gln Glu Asn Met Arg Lys Val Arg
 1               5                  10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 86

Cys Phe Gln Trp Gln Arg Glu Met Arg Lys Val Arg
 1               5                  10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted
<220> FEATURE:
<221> NAME/KEY: MISC_FEATURE
<222> LOCATION: (5)
<223> OTHER INFORMATION: Amino acid 5 is Xaa wherein Xaa = Orn.

<400> SEQUENCE: 87

Cys Phe Gln Trp Xaa Arg Asn Met Arg Lys Val Arg
 1               5                  10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted
<220> FEATURE:
<221> NAME/KEY: MISC_FEATURE
<222> LOCATION: (5)
<223> OTHER INFORMATION: Amino acid 5 is Xaa wherein Xaa = Nle.

<400> SEQUENCE: 88

Cys Phe Gln Trp Xaa Arg Asn Met Arg Lys Val Arg
 1               5                  10

<210> SEQ ID NO 89
<211> LENGTH: 12
<212> TYPE: PRT
<213> ORGANISM: Artificial Sequence
<220> FEATURE:

```
<223> OTHER INFORMATION: Description of Artificial Sequence: of natural
      or artificial origin, corresponding to the sequence
      consisting of aa 20-31 in human lactoferrin
      wherein one aa has been substituted
<220> FEATURE:
<221> NAME/KEY: MISC_FEATURE
<222> LOCATION: (7)
<223> OTHER INFORMATION: Amino acid 7 is Xaa wherein Xaa = Orn.

<400> SEQUENCE: 89

Cys Phe Gln Trp Gln Arg Xaa Met Arg Lys Val Arg
 1               5                  10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted
<220> FEATURE:
<221> NAME/KEY: MISC_FEATURE
<222> LOCATION: (7)
<223> OTHER INFORMATION: Amino acid 7 is Xaa wherein Xaa = Nle.

<400> SEQUENCE: 90

Cys Phe Gln Trp Gln Arg Xaa Met Arg Lys Val Arg
 1               5                  10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein one aa has been substituted

<400> SEQUENCE: 91

Cys Phe Gln Trp Lys Arg Asn Met Arg Lys Val Arg
 1               5                  10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 20-31 in human
      lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (12)
<223> OTHER INFORMATION: AMIDATION

<400> SEQUENCE: 92

Cys Phe Gln Trp Lys Arg Asn Met Arg Lys Val Arg
 1               5                  10

<210> SEQ ID NO 93
<211> LENGTH: 12
<212> TYPE: PRT
<213> ORGANISM: Artificial Sequence
```

```
<220> FEATURE:
<223> OTHER INFORMATION: Description of Artificial Sequence: of natural
      or artificial origin, corresponding to the sequence
      consisting of aa 20-31 in human lactoferrin
      wherein some aa have been substituted

<400> SEQUENCE: 93

Cys Phe Gln Trp Lys Arg Ala Met Arg Lys Val Arg
 1               5                  10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein some aa have been substituted

<400> SEQUENCE: 94

Cys Phe Ala Trp Lys Arg Asn Met Arg Lys Val Arg
 1               5                  10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein some aa have been substituted

<400> SEQUENCE: 95

Cys Phe Ala Trp Gln Arg Ala Met Arg Lys Val Arg
 1               5                  10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20-31 in human lactoferrin
      wherein some aa have been substituted

<400> SEQUENCE: 96

Cys Phe Gln Leu Lys Lys Asn Met Lys Lys Val Arg
 1               5                  10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 18-31 in human
      lactoferrin

<400> SEQUENCE: 97

Cys Phe Ala Leu Lys Lys Ala Met Lys Lys Val Arg
 1               5                  10

<210> SEQ ID NO 98
<211> LENGTH: 14
<212> TYPE: PRT
```

```
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 18-31 in human
      lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 98

Thr Lys Lys Phe Gln Trp Gln Arg Asn Met Arg Lys Val Arg
 1               5                  10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 20-31 in human
      lactoferrin
<220> FEATURE:
<221> NAME/KEY: PEPTIDE
<222> LOCATION: (3)
<223> OTHER INFORMATION: Amino acid 3 is Xaa wherein Xaa = Gln or Ala.
<220> FEATURE:
<221> NAME/KEY: PEPTIDE
<222> LOCATION: (4)
<223> OTHER INFORMATION: Amino acid 4 is Xaa wherein Xaa = Trp or Leu.
<220> FEATURE:
<221> NAME/KEY: PEPTIDE
<222> LOCATION: (5)
<223> OTHER INFORMATION: Amino acid 5 is Xaa wherein Xaa = Gln, Lys,
      Orn, Ala or Nle.
<220> FEATURE:
<221> NAME/KEY: PEPTIDE
<222> LOCATION: (6)
<223> OTHER INFORMATION: Amino acid 6 is Xaa wherein Xaa = Arg, Lys or
      Ala.
<220> FEATURE:
<221> NAME/KEY: PEPTIDE
<222> LOCATION: (7)
<223> OTHER INFORMATION: Amino acid 7 is Xaa wherein Xaa = Asn, Orn, Ala
      or Nle.
<220> FEATURE:
<221> NAME/KEY: PEPTIDE
<222> LOCATION: (8)
<223> OTHER INFORMATION: Amino acid 8 is Xaa wherein Xaa = Met or Leu.
<220> FEATURE:
<221> NAME/KEY: PEPTIDE
<222> LOCATION: (9)
<223> OTHER INFORMATION: Amino acid 9 is Xaa wherein Xaa = Arg or Lys.

<400> SEQUENCE: 99

Cys Phe Xaa Xaa Xaa Xaa Xaa Xaa Xaa Lys Val Arg
 1               5                  10

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: a fragment
      of human lactoferrin consisting of the amino acids in
      positions 12-40

<400> SEQUENCE: 100
```

```
-continued

Val Ser Gln Pro Glu Ala Thr Lys Cys Phe Gln Trp Gln Arg Asn Met
 1               5                  10                  15

Arg Lys Val Arg Gly Pro Pro Val Ser Cys Ile Lys Arg
                20                  25

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: of natural
      or artificial origin, corresponding to modification of the
      sequence consisting of amino acids 16-40 in human lactoferrin of
      SEQ ID NO. 2

<400> SEQUENCE: 101

Gly Pro Pro Val Ser Cys Ile Lys Arg
 1               5

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: of natural
      or artificial origin, not a modification of the sequence
      consisting of amino acids 18-31 in human lactoferrin of SEQ ID NO.
      99

<400> SEQUENCE: 102

Glu Ala Thr Lys
 1
```